United States Patent
Cohen et al.

(10) Patent No.: US 12,404,250 B2
(45) Date of Patent: *Sep. 2, 2025

(54) PARP INHIBITORS FOR TREATING CANCER AND ASTHMA

(71) Applicant: Oregon Health & Science University, Portland, OR (US)

(72) Inventors: Michael Cohen, Portland, OR (US); Ilsa Kirby, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/745,664

(22) Filed: Jun. 17, 2024

(65) Prior Publication Data
US 2024/0409518 A1 Dec. 12, 2024

Related U.S. Application Data

(63) Continuation of application No. 17/272,015, filed as application No. PCT/US2019/047991 on Aug. 23, 2019, now Pat. No. 12,030,858.

(60) Provisional application No. 62/723,410, filed on Aug. 27, 2018.

(51) Int. Cl.
    C07D 239/90 (2006.01)
    C07D 403/12 (2006.01)
    C07D 473/38 (2006.01)

(52) U.S. Cl.
    CPC ......... *C07D 239/90* (2013.01); *C07D 403/12* (2013.01); *C07D 473/38* (2013.01)

(58) Field of Classification Search
    CPC ... C07D 403/12; C07D 401/14; C07D 239/90
    See application file for complete search history.

(56) References Cited

U.S. PATENT DOCUMENTS 8,765,773 B2  7/2014  England et al.
2018/0280356 A1  10/2018  Boserhoff et al.

OTHER PUBLICATIONS

Andersson et al., "Discovery of Ligands for ADP-Ribosyltransferases via Docking-Based Virtual Screening", Journal of Medicinal Chemistry, vol. 55, Issue 17, pp. 7706-7718, 2012.
Mosca et al., "Biological Effects of MC2050, a Quinazoline-Based PARP-1 Inhibitor, in Human Neuroblastoma and EBV-Positive Burkill's Lymphoma Cells", ChemMedChem, 2011, 6, 606-611.
CAS Registry No. 1348191-65-0.
CAS Registry No. 1355882-54-0.
CAS Registry No. 1348207-25-9.
CAS Registry No. 1347346-76-2.
Antolin et al., "Exploring the Effect of PARP-1 Flexibility in Docking Studies, Journal of Molecular Graphics & Modelling", vol. 45, pp. 192-201, 2013.
Kabri et al., "Original quinazoline derivatives displaying antiplasmodial properties, European Journal of Medicinal Chemistry", vol. 45, Issue 2, pp. 616-622, 2010.
La Pietra et al., "Challenging Clinically Unresponsive Medullary Thyroid Cancer: Discover and Pharmacological Activity of Novel RET Inhibitors, European Journal of Medicinal Chemistry", 150 (2018), pp. 491-505.
Turgeon et al., "Newly Discovered and Characterized Antivirulence Compounds Inhibit Bacterial Mono-ADP-Ribosyltransferase Toxins", Antimicrobial Agents and Chemotherapy, Mar. 2011, pp. 983-991.
Kelarev et al., "Synthesis of 2-subsliluled and 2,3-disubsliluled quinazolin-4-Ones containing a sterically hindered phenol residue", Chemistry of Helerocyclic Compounds, vol. 40, Issue 5, pp. 616-621, 2004.
Prokhorov et al., "Combining 3D-QSAR and molecular docking for the virtual screening of PARP inhibitors", Mendeleev Communications, vol. 25, Issue 3, pp. 214-215, 2015.
Frame et al., "Yeast-Based High-Throughput Screen Identifies Plasmodium falciparum Equilibralive Nucleoside Transporter 1 Inhibitors That Kill Malaria Parasites", ACS Chemical Biology, vol. 10, Issue 3, pp. 775-783, 2015.
Jafari et al., "Quinazolinone and quinazoline derivatives: recent structures with potent antimicrobial and cytotoxic activities", Res Pharm Sci. Jan.-Feb. 2016;11(1): 1-14.
Thorsell et al., "Structural Basis for Potency and Promiscuity in Poly(ADP-Ribose) Polymerase (PARP) and Tankyrase Inhibitors", Journal of Medicinal Chemistry, 2017, 60, pp. 1262-1271.
Morgan et al., "Selective Inhibition of PARP10 Using a Chemical Genetics Strategy", Bioorg. Med. Chem. Lett. 25 (2015) 4770-4773.
O'Connell et al., "Identifying Direct Protein Targets of Poly-ADP-ribose Polymerase (PARPs) Using Engineered PARP Variants-orthogonal Nicolinamide Adenine Dinucleolide (NAD+) analogue pairs", Curr Protec Chem Biol, 7: 121-139, 2016.
Chang et al., "Methods in Molecular Biology 1813—ADP-ribosylalion and NAD+ Utilizing Enzymes", Methods and Protocols, pp. 245-252, 2018.
Cohen et al., "Insights into the biogenesis, function, and regulation of ADP-ribosylalion", Nature Chemical Biology, Mar. 2018, vol. 14, pp. 236-243.
Hattori et al., "Rational design of conformationally rislricted quinazolinone inhibitors of poly(ADP-riboise) polymerase", Bioorganic & Medicinal Chemistry Letters, 17, (2007), pp. 5577-5581.
Griffin et al., "Resistance-Modifying Agents. 5.1 Synthesis and Biological Properties of Quinazolinone Inhibitors of the DNA Repair Enzyme Poly(ADP-ribose) Polymerase (PARP)", J_ Med. Chem. 1998, 41, 26, 5247-5256.
Hemalatha et al., "Inhibition of poly(adenosine diphosphate-ribose) polymerase using quinazolinone nucleus", Appl Microbiol Biotechnol (2016) 100:7799-7814.

(Continued)

*Primary Examiner* — Kamal A Saeed
(74) *Attorney, Agent, or Firm* — Lee & Hayes, P.C.

(57) ABSTRACT

Provided are substituted 8-methylquinazolin-4(3H)-one compounds useful as PARP inhibitors for the treatment of cancer and asthma, as well as pharmaceutical compositions comprising them and methods for their synthesis.

20 Claims, 6 Drawing Sheets

Specification includes a Sequence Listing.

(56) References Cited

OTHER PUBLICATIONS

Griffin et al., "Novel Benzimidazole and Quinazolinone Inhibitors of the DNA Repair Enzyme Poly(ADP-ribose) polymerase*", Pharmaceutical Sciences 1996, 2:43-47.

Khan et al., "Recent advances in the structural library of functionalized quinazolineand quinazolinone scaffolds: Synthetic approaches and multifariousapplications", European Journal of Medicinal Chemistry, 76 (2014) 193-244.

Khan et al., "Quinazolines and quinazolinones as ubiquitous structural fragments in medicinal chemistry: An update on the development of syntheticmethods and pharmacological diversification", Bioorg. Med. Chem. 24 (2016) 2361-2381.

Kulcsar et al., "Synthesis and study of new 4-quinazolinone inhibitors of the DNA repair enzyme poly(ADP-ribose) polymerase (PARP)", Arkivoc 2003(v) 121-131.

P11 modifying SPRK2 using 6-a-NAD+

P11 modifying NXF1 using 6-a-NAD+

P11 modifying SPRK2 using NAD+

SEQUENCE LISTING

```
Sequence total quantity: 1
SEQ ID NO: 1            moltype = AA   length = 23
FEATURE                 Location/Qualifiers
REGION                  1..23
                        note = affinity tag with hexahistidine sequence and tobacco
                         etch virus protease cleavage site
source                  1..23
                        mol_type = protein
                        organism = synthetic construct
SEQUENCE: 1
MHHHHHHSSG VDLGTENLYF QSM                                                      23
```

PARP INHIBITORS FOR TREATING CANCER AND ASTHMA

CROSS-REFERENCE TO RELATED APPLICATIONS

This application is a continuation of co-pending U.S. Utility application Ser. No. 17/272,015, filed Feb. 26, 2021, which is the 371 National Phase of International Application No. PCT/US19/47991, filed Aug. 23, 2019, which claims priority to and the benefit of the earlier filing of U.S. Provisional Application No. 62/723,410, filed Aug. 27, 2018. Each of these earlier-filed applications is incorporated by reference herein in its entirety.

INCORPORATION BY REFERENCE OF SEQUENCE LISTING

A computer readable text file, entitled "O046-0048USC1.xml" created on or about Jun. 16, 2024, with a file size of 2,371 bytes, contains the sequence listing for this application and is hereby incorporated by reference in its entirety.

INTRODUCTION

PARPs (Poly-ADP-ribose polymerases also known as ADP-ribosyltransferases) are emerging as major effectors of NAD+-mediated signaling in cells. They are a diverse family of 17 mammalian enzymes (PARPs1-17) that catalyze the reversible post-translational modification known as ADP-ribosylation, which involves the transfer of ADP-ribose from NAD+ to target proteins. PARPs can be divided into two subfamilies: i. PARPs that catalyze poly-ADP-ribosylation (PARP1-5; H-Y-E triad motif-containing PARPs, where the glutamate in the third position of the triad is essential for poly-ADP-ribosylation activity), and ii. PARPs that exclusively catalyze mono-ADP-ribosylation (PARP6-8, 10-12, 14-16; H-Y-Φ triad motif-containing PARPs, where Φ is a hydrophobic amino acid instead of a glutamate). While recent studies demonstrate that H-Y-Φ PARPs play pivotal roles in diverse cell processes (e.g., PARP16-unfolded protein response and PARP6-dendritic branching in neurons), the majority of this subfamily remains uncharacterized. As a consequence, the cellular role of mono-ADP-ribosylation is poorly understood. This is due, in large part, to the lack of potent, membrane-permeable inhibitors of H-Y-Φ PARP family members.

There remains a need for selective inhibitors of H-Y-Φ PARPs, as most inhibitors cannot distinguish between H-Y-E and H-Y-Φ PARPs.

SUMMARY OF THE INVENTION

Provided herein is an embodiment comprising a compound of Formula I, or a pharmaceutically acceptable salt thereof:

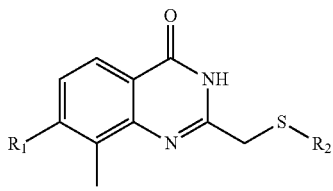

Formula I wherein $R_1$ is selected from $C_1$-$C_3$ alkyl, $C_2$-$C_3$ alkenyl, and $C_2$-$C_3$ alkynyl; and $R_2$ is selected from a phenyl ring and a 3-membered to 10-membered aromatic, partially unsaturated, or unsaturated heterocycle containing 1, 2, 3, or 4 ring nitrogen atoms, with the phenyl ring and the 5- to 10-membered aromatic, partially unsaturated, or unsaturated heterocycle being substituted by 0, 1, 2 or 3 substituents selected from the group of Cl, F, Br, I, OH, $C_1$-$C_6$ alkyl, —O-$C_1$-$C_6$ alkyl, —NH$_2$, —NH($C_1$-$C_6$ alkyl), —N($C_1$-$C_6$ alkyl)$_2$, —CO$_2$H, —CO$_2$($C_1$-$C_6$ alkyl), —CO$_2$-phenyl, and —CO$_2$-benzyl; wherein the phenyl and benzyl rings of the $R_2$—CO$_2$-phenyl, —CO$_2$-benzyl groups are substituted by 0, 1, 2, or 3 substituents selected from the group of Cl, F, Br, I, OH, $C_1$-$C_6$ alkyl, —O-$C_1$-$C_6$ alkyl, —NH$_2$, —NH($C_1$-$C_6$ alkyl), and —N($C_1$-$C_6$ alkyl)$_2$.

Also provided herein are pharmaceutical compositions and methods of treatment utilizing a compound of Formula I, as defined above, or a pharmaceutically acceptable salt thereof.

DETAILED DESCRIPTION OF THE INVENTION

Figure 1:
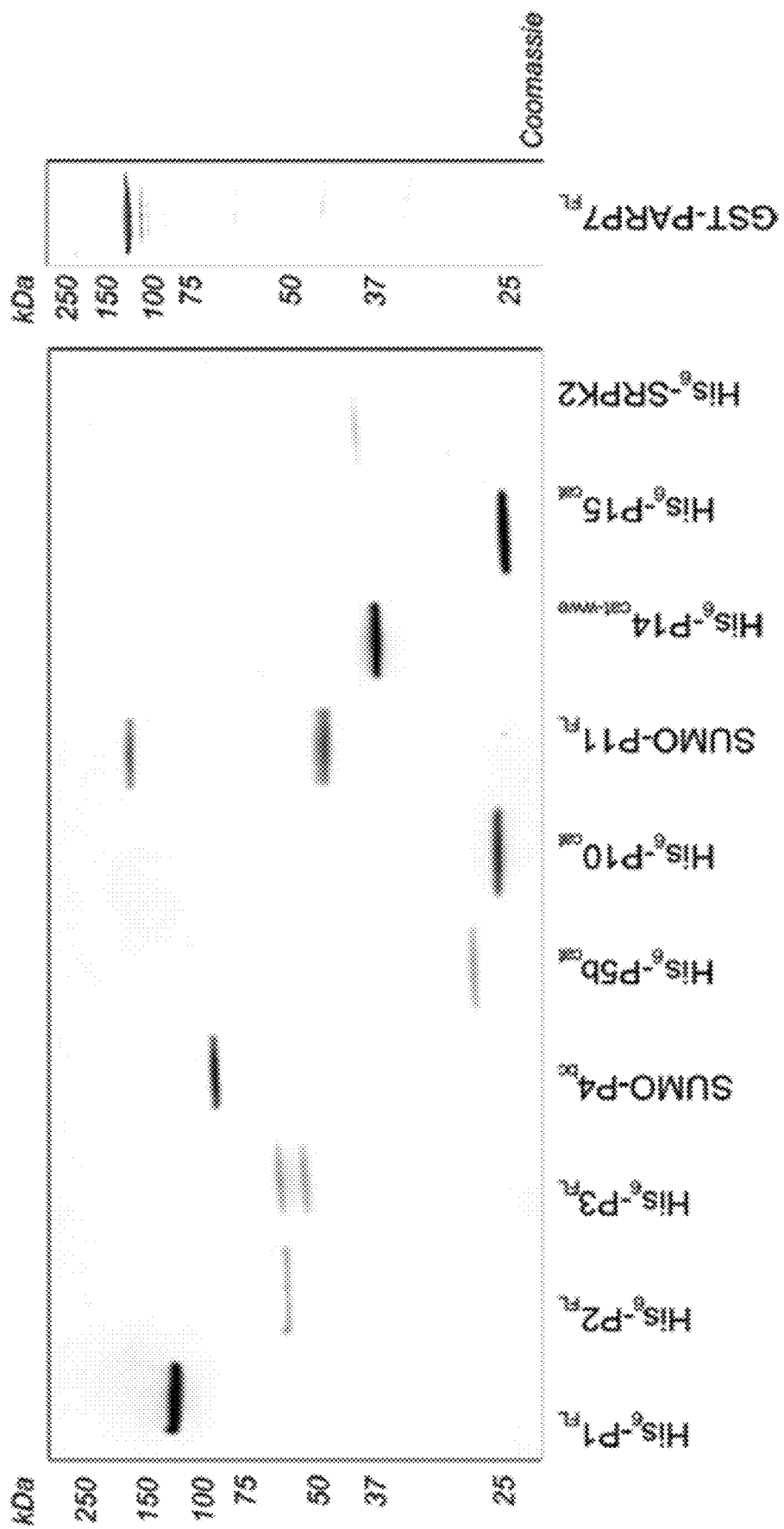
FIG. 1 provides a comparative purity of all proteins used wherein samples were run in a 4-20% gradient SDS-PAGE gel (Bio-Rad) and imaged for Coomassie staining on a ChemiDoc MP system (Bio-Rad).

Also provided is an embodiment comprising a compound of Formula I, or a pharmaceutically acceptable salt thereof:

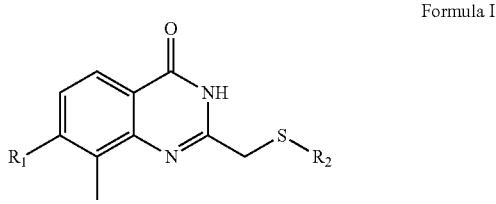

Formula I wherein $R_1$ is selected from the group of $C_1$-$C_3$ alkyl, $C_2$-$C_3$ alkenyl, and $C_2$-$C_3$ alkynyl; and $R_2$ is selected from the group of a phenyl ring and a 5- to 10-membered aromatic or partially unsaturated heterocycle containing 1, 2, 3, or 4 ring nitrogen atoms, wherein the phenyl ring and the 5- to 10-membered aromatic, partially unsaturated, or unsaturated heterocycle are each independently substituted by 0, 1, 2, or 3 substituents selected from the group of Cl, F, Br, I, OH, $C_1$-$C_6$ alkyl, —O-$C_1$-$C_6$ alkyl, —$NH_2$, —NH($C_1$-$C_6$ alkyl), —N($C_1$-$C_6$ alkyl)$_2$, —$CO_2$H, —$CO_2$($C_1$-$C_6$ alkyl), —$CO_2$-phenyl, and —$CO_2$-benzyl; wherein the phenyl and benzyl rings of the $R_2$—$CO_2$-phenyl, —$CO_2$-benzyl groups are substituted by 0, 1, 2, or 3 substituents selected from the group of Cl, F, Br, I, OH, $C_1$-$C_6$ alkyl, —O-$C_1$-$C_6$ alkyl, —$NH_2$, —NH($C_1$-$C_6$ alkyl), and —N($C_1$-$C_6$ alkyl)$_2$.

Another embodiment provides a compound of Formula I, or a pharmaceutically acceptable salt thereof, wherein $R_1$ is selected from $C_1$-$C_2$ alkyl, $C_2$-$C_3$ alkenyl, and $C_2$-$C_3$ alkynyl; and $R_2$ is as defined above.

Another embodiment provides a compound of Formula I, or a pharmaceutically acceptable salt thereof, wherein $R_1$ is selected from $CH_3$, $C_2$-$C_3$ alkenyl, and $C_2$-$C_3$ alkynyl; and $R_2$ is as defined above.

Another embodiment provides a compound of Formula I, or a pharmaceutically acceptable salt thereof, wherein $R_1$ is selected from $CH_3$, —CH=CH2, and $C_2$-$C_3$ alkynyl; and $R_2$ is as defined above.

Another embodiment provides a compound of Formula I, or a pharmaceutically acceptable salt thereof, wherein $R_1$ is selected from $CH_3$, —CH=$CH_2$, and —C≡C—$CH_3$; and $R_2$ is as defined above.

Another embodiment provides a compound of Formula I, or a pharmaceutically acceptable salt thereof, wherein $R_1$ is $CH_3$; and $R_2$ is as defined above.

Another embodiment provides a compound of Formula I, or a pharmaceutically acceptable salt thereof, wherein $R_1$ is —C≡C—$CH_3$; and $R_2$ is as defined above.

Further provided is an embodiment comprising a compound of Formula I, or a pharmaceutically acceptable salt thereof:

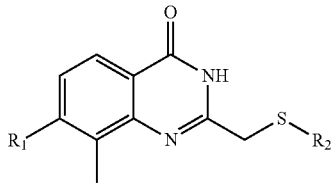

Formula I wherein $R_1$ is selected from the group of $C_1$-$C_3$ alkyl, $C_2$-$C_3$ alkenyl, and $C_2$-$C_3$ alkynyl; and $R_2$ is selected from the group of a phenyl ring and a 5- to 10-membered aromatic or partially unsaturated heterocycle containing 1, 2, 3, or 4 ring nitrogen atoms, wherein the phenyl ring and the 5- to 10-membered aromatic, partially unsaturated, or unsaturated heterocycle are each independently substituted by 0, 1, 2, or 3 substituents selected from the group of OH, $C_1$-$C_6$ alkyl, —O-$C_1$-$C_6$ alkyl, —$NH_2$, —NH($C_1$-$C_6$ alkyl), —N($C_1$-$C_6$ alkyl)$_2$, —$CO_2$H, —$CO_2$($C_1$-$C_6$ alkyl), —$CO_2$-phenyl, and —$CO_2$-benzyl; wherein the phenyl and benzyl rings of the $R_2$—$CO_2$-phenyl, —$CO_2$-benzyl groups are substituted by 0, 1, 2, or 3 substituents selected from the group of Cl, F, Br, I, OH, $C_1$-$C_6$ alkyl, —O-$C_1$-$C_6$ alkyl, —$NH_2$, —NH($C_1$-$C_6$ alkyl), and —N($C_1$-$C_6$ alkyl)$_2$.

Another embodiment provides a compound of Formula I, or a pharmaceutically acceptable salt thereof, wherein $R_1$ is selected from $C_1$-$C_2$ alkyl, $C_2$-$C_3$ alkenyl, and $C_2$-$C_3$ alkynyl; and $R_2$ is as defined above.

Another embodiment provides a compound of Formula I, or a pharmaceutically acceptable salt thereof, wherein $R_1$ is selected from $CH_3$, $C_2$-$C_3$ alkenyl, and $C_2$-$C_3$ alkynyl; and $R_2$ is as defined above.

Another embodiment provides a compound of Formula I, or a pharmaceutically acceptable salt thereof, wherein $R_1$ is selected from $CH_3$, —CH=CH2, and $C_2$-$C_3$ alkynyl; and $R_2$ is as defined above.

Another embodiment provides a compound of Formula I, or a pharmaceutically acceptable salt thereof, wherein $R_1$ is selected from $CH_3$, —CH=$CH_2$, and —C≡C—$CH_3$; and $R_2$ is as defined above.

Another embodiment provides a compound of Formula I, or a pharmaceutically acceptable salt thereof, wherein $R_1$ is $CH_3$; and $R_2$ is as defined above.

Another embodiment provides a compound of Formula I, or a pharmaceutically acceptable salt thereof, wherein $R_1$ is —C≡C—$CH_3$; and $R_2$ is as defined above.

Further provided is an embodiment comprising a compound of Formula II, or a pharmaceutically acceptable salt thereof:

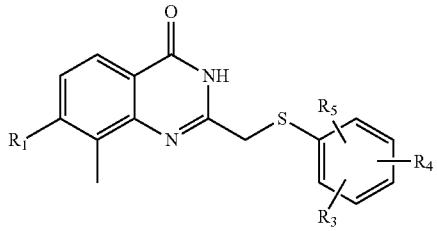

Formula II wherein $R_1$ is selected from the group of $C_1$-$C_3$ alkyl, $C_2$-$C_3$ alkenyl, and $C_2$-$C_3$ alkynyl; and $R_3$, $R_4$, and $R_5$ are each independently selected from the group of OH, $C_1$-$C_6$ alkyl, —O-$C_1$-$C_6$ alkyl, —$NH_2$, —NH($C_1$-$C_6$ alkyl), —N($C_1$-$C_6$ alkyl)$_2$, —$CO_2$H, —$CO_2$($C_1$-$C_6$ alkyl), —$CO_2$-phenyl, and —$CO_2$-benzyl; wherein the phenyl and benzyl rings of the $R_3$, $R_4$, and $R_5$—$CO_2$-phenyl and —$CO_2$-benzyl groups are substituted by 0, 1, 2, or 3 substituents selected from the group of Cl, F, Br, I, OH, $C_1$-$C_6$ alkyl, —O-$C_1$-$C_6$ alkyl, —$NH_2$, —NH($C_1$-$C_6$ alkyl), and —N($C_1$-$C_6$ alkyl)$_2$.

Another embodiment provides a compound of Formula II, or a pharmaceutically acceptable salt thereof, wherein $R_1$ is selected from $C_1$-$C_2$ alkyl, $C_2$-$C_3$ alkenyl, and $C_2$-$C_3$ alkynyl; and $R_3$, $R_4$, and $R_5$ are as defined above.

Another embodiment provides a compound of Formula II, or a pharmaceutically acceptable salt thereof, wherein $R_1$ is selected from $CH_3$, $C_2$-$C_3$ alkenyl, and $C_2$-$C_3$ alkynyl; and $R_3$, $R_4$, and $R_5$ are as defined above.

Another embodiment provides a compound of Formula II, or a pharmaceutically acceptable salt thereof, wherein $R_1$ is selected from $CH_3$, —CH=CH2, and $C_2$-$C_3$ alkynyl; and $R_3$, $R_4$, and $R_5$ are as defined above.

Another embodiment provides a compound of Formula II, or a pharmaceutically acceptable salt thereof, wherein $R_1$ is selected from $CH_3$, —CH=$CH_2$, and —C≡C—$CH_3$; and $R_3$, $R_4$, and $R_5$ are as defined above.

Another embodiment provides a compound of Formula II, or a pharmaceutically acceptable salt thereof, wherein $R_1$ is $CH_3$; and $R_3$, $R_4$, and $R_5$ are as defined above.

Another embodiment provides a compound of Formula II, or a pharmaceutically acceptable salt thereof, wherein $R_1$ is —C≡C—$CH_3$; and $R_3$, $R_4$, and $R_5$ are as defined above.

For each embodiment described above for a compound of Formula II, or a pharmaceutically acceptable salt thereof, there is provided another embodiment wherein $R_1$, $R_3$, and $R_4$ are as defined for the initial embodiment referenced and $R_5$ is hydrogen.

For each embodiment described above for a compound of Formula II, or a pharmaceutically acceptable salt thereof, there is provided an additional embodiment wherein $R_1$ and $R_3$, are as defined for the initial embodiment referenced and $R_4$ and $R_5$ are both hydrogen.

For each embodiment described above for a compound of Formula II, or a pharmaceutically acceptable salt thereof, there is provided an additional embodiment wherein $R_1$ is as defined for the initial embodiment referenced and $R_3$, $R_4$, and $R_5$ are each hydrogen.

Further provided is a compound of Formula III, or a pharmaceutically acceptable salt thereof:

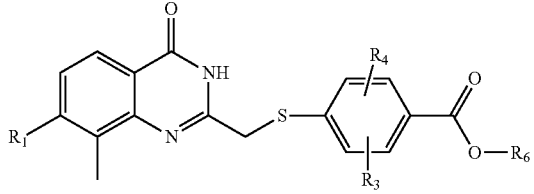

Formula III wherein $R_1$ is selected from the group of $C_1$-$C_3$ alkyl, $C_2$-$C_3$ alkenyl, and $C_2$-$C_3$ alkynyl; and
$R_3$ and $R_4$ are each independently selected from the group of H, OH, $C_1$-$C_6$ alkyl, —O-$C_1$-$C_6$ alkyl, —$NH_2$, —NH($C_1$-$C_6$ alkyl), —N($C_1$-$C_6$ alkyl)$_2$, —$CO_2H$, —$CO_2$($C_1$-$C_6$ alkyl), —$CO_2$-phenyl, and —$CO_2$-benzyl;
wherein the $R_6$ is selected from the group of H, $C_1$-$C_6$ alkyl, phenyl, and benzyl, wherein the rings of the phenyl and benzyl groups are substituted by 0, 1, 2, or 3, substituents selected from the group of Cl, F, Br, I, OH, $C_1$-$C_6$ alkyl, —O-$C_1$-$C_6$ alkyl, —$NH_2$, —NH($C_1$-$C_6$ alkyl), and —N($C_1$-$C_6$ alkyl)$_2$.

Another embodiment provides a compound of Formula III, or a pharmaceutically acceptable salt thereof, wherein $R_1$ is selected from $C_1$-$C_2$ alkyl, $C_2$-$C_3$ alkenyl, and $C_2$-$C_3$ alkynyl; and $R_2$ is as defined above.

Another embodiment provides a compound of Formula III, or a pharmaceutically acceptable salt thereof, wherein $R_1$ is selected from $CH_3$, $C_2$-$C_3$ alkenyl, and $C_2$-$C_3$ alkynyl; and $R_2$ is as defined above.

Another embodiment provides a compound of Formula III, or a pharmaceutically acceptable salt thereof, wherein $R_1$ is selected from $CH_3$, —CH═CH2, and $C_2$-$C_3$ alkynyl; and $R_2$ is as defined above.

Another embodiment provides a compound of Formula III, or a pharmaceutically acceptable salt thereof, wherein $R_1$ is selected from $CH_3$, —CH═$CH_2$, and —C≡C—$CH_3$; and $R_2$ is as defined above.

Another embodiment provides a compound of Formula III, or a pharmaceutically acceptable salt thereof, wherein $R_1$ is $CH_3$; and $R_2$ is as defined above.

Another embodiment provides a compound of Formula III, or a pharmaceutically acceptable salt thereof, wherein $R_1$ is —C≡C—$CH_3$; and $R_2$ is as defined above.

For each embodiment described above for a compound of Formula III, or a pharmaceutically acceptable salt thereof, there is provided another embodiment wherein $R_1$, $R_3$, and $R_6$ are as defined for the initial embodiment referenced and $R_4$ is hydrogen.

For each embodiment described above for a compound of Formula III, or a pharmaceutically acceptable salt thereof, there is provided another embodiment wherein $R_1$ and $R_6$ are as defined for the initial embodiment referenced and $R_3$ and $R_4$ are both hydrogen.

Additionally provided is a compound of Formula IV, or a pharmaceutically acceptable salt thereof:

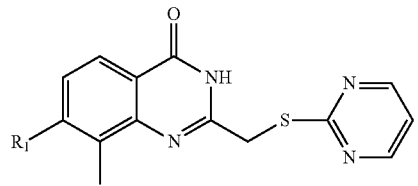

Formula IV wherein $R_1$ is selected from the group of $C_1$-$C_3$ alkyl, $C_2$-$C_3$ alkenyl, and $C_2$-$C_3$ alkynyl.

Another embodiment provides a compound of Formula IV, or a pharmaceutically acceptable salt thereof, wherein $R_1$ is selected from $C_1$-$C_2$ alkyl, $C_2$-$C_3$ alkenyl, and $C_2$-$C_3$ alkynyl.

Another embodiment provides a compound of Formula IV, or a pharmaceutically acceptable salt thereof, wherein $R_1$ is selected from $CH_3$, $C_2$-$C_3$ alkenyl, and $C_2$-$C_3$ alkynyl.

Another embodiment provides a compound of Formula IV, or a pharmaceutically acceptable salt thereof, wherein $R_1$ is selected from $CH_3$, —CH═CH2, and $C_2$-$C_3$ alkynyl.

Another embodiment provides a compound of Formula IV, or a pharmaceutically acceptable salt thereof, wherein $R_1$ is selected from $CH_3$, —CH═$CH_2$, and —C≡C—$CH_3$.

Another embodiment provides a compound of Formula IV, or a pharmaceutically acceptable salt thereof, wherein $R_1$ is $CH_3$.

Another embodiment provides a compound of Formula IV, or a pharmaceutically acceptable salt thereof, wherein $R_1$ is —C≡C—$CH_3$.

Additionally provided is a compound of Formula V, or a pharmaceutically acceptable salt thereof:

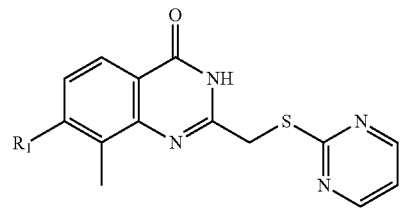

Formula V wherein $R_1$ is selected from the group of $C_1$-$C_3$ alkyl, $C_2$-$C_3$ alkenyl, and $C_2$-$C_3$ alkynyl.

Another embodiment provides a compound of Formula V, or a pharmaceutically acceptable salt thereof, wherein $R_1$ is selected from $C_1$-$C_2$ alkyl, $C_2$-$C_3$ alkenyl, and $C_2$-$C_3$ alkynyl.

Another embodiment provides a compound of Formula V, or a pharmaceutically acceptable salt thereof, wherein $R_1$ is selected from $CH_3$, $C_2$-$C_3$ alkenyl, and $C_2$-$C_3$ alkynyl.

Another embodiment provides a compound of Formula V, or a pharmaceutically acceptable salt thereof, wherein $R_1$ is selected from $CH_3$, —CH=CH2, and $C_2$-$C_3$ alkynyl.

Another embodiment provides a compound of Formula V, or a pharmaceutically acceptable salt thereof, wherein $R_1$ is selected from $CH_3$, —CH=CH$_2$, and —C≡C—CH$_3$.

Another embodiment provides a compound of Formula V, or a pharmaceutically acceptable salt thereof, wherein $R_1$ is $CH_3$.

Another embodiment provides a compound of Formula V, or a pharmaceutically acceptable salt thereof, wherein $R_1$ is —C≡C—CH$_3$.

Additionally provided is a compound of Formula VI, or a pharmaceutically acceptable salt thereof:

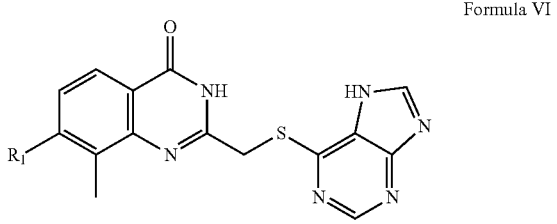

Formula VI wherein $R_1$ is selected from the group of $C_1$-$C_3$ alkyl, $C_2$-$C_3$ alkenyl, and $C_2$-$C_3$ alkynyl.

Another embodiment provides a compound of Formula VI, or a pharmaceutically acceptable salt thereof, wherein $R_1$ is selected from $C_1$-$C_2$ alkyl, $C_2$-$C_3$ alkenyl, and $C_2$-$C_3$ alkynyl.

Another embodiment provides a compound of Formula VI, or a pharmaceutically acceptable salt thereof, wherein $R_1$ is selected from $CH_3$, $C_2$-$C_3$ alkenyl, and $C_2$-$C_3$ alkynyl.

Another embodiment provides a compound of Formula VI, or a pharmaceutically acceptable salt thereof, wherein $R_1$ is selected from $CH_3$, —CH=CH2, and $C_2$-$C_3$ alkynyl.

Another embodiment provides a compound of Formula VI, or a pharmaceutically acceptable salt thereof, wherein $R_1$ is selected from $CH_3$, —CH=CH$_2$, and —C≡C—CH$_3$.

Another embodiment provides a compound of Formula VI, or a pharmaceutically acceptable salt thereof, wherein $R_1$ is $CH_3$.

Another embodiment provides a compound of Formula VI, or a pharmaceutically acceptable salt thereof, wherein $R_1$ is —C≡C—CH$_3$.

Additionally provided is a compound of Formula VII, or a pharmaceutically acceptable salt thereof:

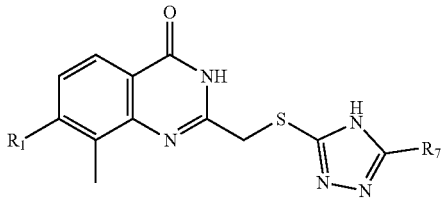

Formula VII wherein $R_1$ is selected from the group of $C_1$-$C_3$ alkyl, $C_2$-$C_3$ alkenyl, and $C_2$-$C_3$ alkynyl; and $R_7$ is selected from the group of H, —CH$_3$, —NH$_2$, —NH($C_1$-$C_6$ alkyl), and —N($C_1$-$C_6$ alkyl)$_2$.

Another embodiment provides a compound of Formula VII, or a pharmaceutically acceptable salt thereof, wherein $R_1$ is selected from $C_1$-$C_2$ alkyl, $C_2$-$C_3$ alkenyl, and $C_2$-$C_3$ alkynyl; and $R_7$ is as defined above.

Another embodiment provides a compound of Formula VII, or a pharmaceutically acceptable salt thereof, wherein $R_1$ is selected from $CH_3$, $C_2$-$C_3$ alkenyl, and $C_2$-$C_3$ alkynyl; and $R_7$ is as defined above.

Another embodiment provides a compound of Formula VII, or a pharmaceutically acceptable salt thereof, wherein $R_1$ is selected from $CH_3$, —CH=CH2, and $C_2$-$C_3$ alkynyl; and $R_7$ is as defined above.

Another embodiment provides a compound of Formula VII, or a pharmaceutically acceptable salt thereof, wherein $R_1$ is selected from $CH_3$, —CH=CH$_2$, and —C≡C—CH$_3$; and $R_7$ is as defined above.

Another embodiment provides a compound of Formula VII, or a pharmaceutically acceptable salt thereof, wherein $R_1$ is $CH_3$; and $R_7$ is as defined above.

Another embodiment provides a compound of Formula VII, or a pharmaceutically acceptable salt thereof, wherein $R_1$ is —C≡C—CH$_3$; and $R_7$ is as defined above.

Within each of the compound description groups herein concerning Formula I, Formula II, Formula III, Formula IV, Formula V, and Formula VII (Formulas I-VII), there is a further embodiment in which the variable $R_1$ is $C_1$-$C_3$ alkyl and all other variables are as described for the individual embodiments of the group.

Within each of the compound description groups herein concerning Formulas I-VII, there is a further embodiment in which the variable $R_1$ is —CH$_3$ and all other variables are as described for the individual embodiments of the group.

Within each of the compound description groups herein concerning Formulas I-VII, there is a further embodiment in which the variable $R_1$ is $C_2$-$C_3$ alkenyl and all other variables are as described for the individual embodiments of the group.

Within each of the compound description groups herein concerning Formulas I-VII, there is a further embodiment in which the variable $R_1$ is $C_2$-$C_3$ alkynyl and all other variables are as described for the individual embodiments of the group.

Examples of nitrogen-containing rings at $R_2$ in the descriptions herein include the following:

Examples of 3-membered to 10-membered nitrogen-containing rings at $R_2$ in the descriptions herein include: 3-membered azirinyl and aziridinyl rings; 4-membered azetyl and 1,2-dihydroazetyl, 5-membered pyrrolidinyl, 2,5-dihydro-1H-pyrrolyl, 2,3-dihydro-1H-pyrrolyl, imidazolyl, pyrazolyl, 1H-1, 2, 4-triazolyl, 4H-1, 2, 4-triazolyl, 1H-1, 2, 3-triazolyl, and 2H-1, 2, 3-triazolyl rings; 6-membered piperidinyl, 1,2,3,4-tetrahydropyridinyl, 1,2,3,6-tetrahydropyridinyl, pyridinyl, pyridazinyl, pyrimidinyl, pyrazinyl, 1,2,3-triazinyl, 1,2,4,-triazinyl, 1,3,5-triazinyl, 1,2,3,5-tetrazinyl, 1,2,4,5-tetrazinyl rings, and pentazinyl rings; 7-membered azepanyl, azepinal (including 2,3,4,5-tetrahydro-1H-azepinyl, 2,3,4,7-tetrahydro-1H-azepinyl, and 2,3,6,7-tetrahydro-1H-azepinyl), 1,2-diazepinyl, 1,3-diazepinyl, and 1,4-diazepinyl rings; 9-membered indolinyl, 1-H-Indolyl, 3H-indolyl, 2H-isoindolyl, indolizinyl, 1H-indazolyl, benzimidazolyl, 7-azaindolyl, 4-azaindolyl, 5-azaindolyl, 6-azaindolyl, 7-azaindazolyl, pyrazolo[1,5-a]pyrmindinyl, and purinyl rings; and 10-membered 1,2-dihydroquinolinyl, 1,2-isoquinolinyl, dihydroisoquinolinyl, quinolinyl, quinoxalinyl, phthalazinyl, quinazolinyl, decahydroisoquinoline, decahydroquinoline, 1,2,3,4-tetrahydroquinoline, cinnolinyl, 1,8-naphthyridinyl, pyrido[3,2-d]pyrimidinyl, pyrido[4,3-d]pyrimidinyl, pyrido[3,4-pyrazinyl, pyrido[2,3-b]pyrazinyl, and pteridinyl rings.

Also described for a compound of Formulas I, II, III, IV, V, VI, and VII, as well as the individual compounds disclosed herein, are the pharmaceutically acceptable salts, pharmaceutically acceptable co-crystals, pharmaceutically acceptable esters, pharmaceutically acceptable solvates, hydrates, isomers (including optical isomers, racemates, or other mixtures thereof), tautomers, isotopes, polymorphs, and pharmaceutically acceptable prodrugs of such compounds.

The compounds herein may possess an asymmetric center, and can be produced as a racemic mixture or as individual enantiomers. The individual enantiomers may be obtained by asymmetric synthesis or by resolving a racemic or non-racemic mixture of an intermediate at some appropriate stage of the synthesis. The individual enantiomers may also be obtained by resolution of the compound by conventional means, such as crystallization in the presence of a resolving agent, or chromatography, using, for example a chiral high-pressure liquid chromatography (HPLC) column. The individual enantiomers as well as racemic and non-racemic mixtures of enantiomers are within the scope of the present disclosure, all of which are intended to be included within the structures depicted in this specification unless otherwise specifically indicated.

Definitions

The term "alkyl" refers to a straight or branched hydrocarbon. For example, an alkyl group can have 1 to 20 carbon atoms (i.e., $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, and octyl (-($CH_2$)$_7CH_3$).

The term "alkoxy" refers to a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—C($CH_3$)$_3$ or —OtBu) and the like.

The term "alkenyl" refers to a straight or branched hydrocarbon with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—CH2CH=$CH_2$), cyclopentenyl (—$C_5H_7$), and 5-hexenyl (—$CH_2CH_2CH_2CH_2$CH=$CH_2$).

The term "alkynyl" refers to a straight or branched hydrocarbon with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargylic (—$CH_2$C≡CH), and the like.

The term "heterocycle" or "heterocyclyl" as used herein includes by way of example and not limitation those heterocycles described in Paquette, Leo A.; Principles of Modern Heterocyclic Chemistry (W. A. Benjamin, New York, 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and J. Am. Chem. Soc. (1960) 82:5566. In one specific embodiment of the invention "heterocycle" includes a "carbocycle" as defined herein, wherein one or more (e.g., 1, 2, 3, or 4) carbon atoms have been replaced with a heteroatom (e.g., O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups The acronym "PARP" refers to an enzyme of the poly ADP ribose polymerase group of family.

"Pharmaceutically acceptable salts", as used herein, includes, for example, salts with inorganic acids and salts with an organic acid. Examples of salts may include hydrochloride, phosphate, diphosphate, hydrobromide, sulfate, sulfinate, nitrate, malate, maleate, fumarate, tartrate, succinate, citrate, acetate, lactate, methanesulfonate (mesylate), benzenesuflonate (besylate), p-toluenesulfonate (tosylate), 2-hydroxyethylsulfonate, benzoate, salicylate, stearate, and alkanoate (such as acetate, HOOC-($CH_2$)$_n$-COOH where n is 0-4). In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

Also provided herein are pharmaceutical compositions comprising a pharmaceutically effective amount of a compound described herein, or a pharmaceutically acceptable salt thereof, and a pharmaceutically acceptable carrier.

The terms "therapeutically effective amount" or "pharmaceutically effective amount" refers to an amount that is sufficient to effect treatment, as defined below, when administered to a subject (e.g., a mammal, such as a human) in need of such treatment. The therapeutically or pharmaceutically effective amount will vary depending upon the subject and disease condition being treated, the weight and age of the subject, the severity of the disease condition, the manner of administration and the like, which can readily be determined by one of ordinary skill in the art. For example, a "therapeutically effective amount" or a "pharmaceutically effective amount" of a compound of Formula I (including those of Formulas II, III, IV, V, VI, and VII), or a pharmaceutically acceptable salt or co-crystal thereof, is an amount sufficient to modulate the activity in question, and thereby treat a subject (e.g., a human) suffering an indication, or to ameliorate or alleviate the existing symptoms of the indication. For example, a therapeutically or pharmaceutically effective amount may be an amount sufficient to decrease a symptom of a disease or condition responsive to inhibition activity of one or more PARPs.

A pharmaceutically effective amount of a compound herein may be determined by a medical practitioner. Ranges of pharmaceutically effective amounts of the compounds herein include from about 0.1 mg to about 1,000 mg, from about 1 mg to about 500 mg, from about 1 mg to about 400 mg, from about 1 mg to about 300 mg, from about 1 mg to about 200 mg, from about 1 mg to about 100 mg, from about 1 mg to about 50 mg, from about 50 mg to about 100 mg, from about 100 mg to about 200 mg, from about 100 mg to about 500 mg, and from about 500 mg to about 1,000 mg per dose.

Provided herein is a method of inhibiting the activity of a PARP enzyme in a human, the method comprising administering to the human in need thereof a pharmaceutically effective amount of a compound of Formula I, or a pharmaceutically acceptable salt thereof.

Provided herein is a method of treatment of an advanced hematological malignancy in a human, the method comprising administering to the human in need thereof a pharmaceutically effective amount of a compound of Formula I, or a pharmaceutically acceptable salt thereof. Examples of advanced hematological malignancies include advanced forms of leukemia, myelodysplastic syndrome, multiple myeloma, Hodgkin's disease (HD), or Non-Hodgkin's lymphoma (NHL). The leukemias in question may be those of the group of chronic myeloid leukemia (CML), acute myeloid leukemia (AML), acute lymphocytic leukemia (ALL), chronic lymphocytic leukemia (CLL), and chronic myelomonocytic leukemia (CMML).

Provided herein is a method of treatment of an advanced or recurrent solid tumors in a human, the method comprising administering to the human in need thereof a pharmaceutically effective amount of a compound of Formula I, or a pharmaceutically acceptable salt thereof.

Provided herein is a method of treatment of ovarian cancer in a human, the method comprising administering to the human in need thereof a pharmaceutically effective amount of a compound of Formula I, or a pharmaceutically acceptable salt thereof.

Provided herein is a method of treatment of advanced ovarian cancer in a human, the method comprising administering to the human in need thereof a pharmaceutically effective amount of a compound of Formula I, or a pharmaceutically acceptable salt thereof.

Provided herein is a method of treatment of metastatic ovarian cancer in a human, the method comprising administering to the human in need thereof a pharmaceutically effective amount of a compound of Formula I, or a pharmaceutically acceptable salt thereof.

Provided herein is a method of treatment of breast cancer in a human, the method comprising administering to the human in need thereof a pharmaceutically effective amount of a compound of Formula I, or a pharmaceutically acceptable salt thereof.

Provided herein is a method of treatment of triple-negative breast cancer in a human, the method comprising administering to the human in need thereof a pharmaceutically effective amount of a compound of Formula I, or a pharmaceutically acceptable salt thereof.

Provided herein is a method of treatment of metastatic breast cancer in a human, the method comprising administering to the human in need thereof a pharmaceutically effective amount of a compound of Formula I, or a pharmaceutically acceptable salt thereof.

Provided herein is a method of treatment of non-small cell lung cancer in a human, the method comprising administering to the human in need thereof a pharmaceutically effective amount of a compound of Formula I, or a pharmaceutically acceptable salt thereof.

Provided herein is a method of treatment of melanoma in a human, the method comprising administering to the human in need thereof a pharmaceutically effective amount of a compound of Formula I, or a pharmaceutically acceptable salt thereof.

Provided herein is a method of treatment of metastatic melanoma in a human, the method comprising administering to the human in need thereof a pharmaceutically effective amount of a compound of Formula I, or a pharmaceutically acceptable salt thereof.

Provided herein is a method of treatment of colorectal cancer in a human, the method comprising administering to the human in need thereof a pharmaceutically effective amount of a compound of Formula I, or a pharmaceutically acceptable salt thereof.

Provided herein is a method of treatment of metastatic colorectal cancer in a human, the method comprising administering to the human in need thereof a pharmaceutically effective amount of a compound of Formula I, or a pharmaceutically acceptable salt thereof.

The compounds and pharmaceutical compositions described herein may be used in the treatment of conditions. In one embodiment of the first aspect, the ER stress-related condition is a cancer, protein folding/misfolding disease, diabetes mellitus, Wolcott-Rallison syndrome, ischemia/reperfusion injury, stroke, neurodegeneration, atherosclerosis, neoplasia, hypoxia, or hypoglycemia. Cancers which may be treated with compounds herein includes colon adenocarcinoma, esophagus adenocarcinoma, liver hepatocellular carcinoma, squamous cell carcinoma, pancreas adenocarcinoma, islet cell tumor, rectum adenocarcinoma, gastrointestinal stromal tumor, stomach adenocarcinoma, adrenal cortical carcinoma, follicular carcinoma, papillary carcinoma, breast cancer, ductal carcinoma, lobular carcinoma, intraductal carcinoma, mucinous carcinoma, Phyllodes tumor, Ewing's sarcoma, ovarian adenocarcinoma, endometrium adenocarcinoma, granulose cell tumor, mucinous cystadenocarcinoma, cervix adenocarcinoma, vulva squamous cell carcinoma, basal cell carcinoma, prostate adenocarcinoma, giant cell tumor of bone, bone osteosarcoma, larynx carcinoma, lung adenocarcinoma, kidney carcinoma, urinary bladder carcinoma, Wilm's tumor, and lymphoma. Protein folding/misfolding diseases include Huntington's disease, spinobulbar muscular atrophy (Kennedy disease), Machado-Joseph disease, dentatorubral-pallidoluysian atrophy (Haw River Syndrome), spinocerebellar ataxia, Alzheimer's disease, Parkinson's disease, amyotrophic lateral sclerosis (ALS), Creutzfeldt-Jakob disease, bovine spongiform encephalopathy (BSE), light chain amyloidosis (AL), heavy chain amyloidosis (AH), secondary amyloidosis (AA), aortic medial amyloidosis, ApoA1, ApoAII, ad ApoAIV amyloidosis, insulin amyloidosis, cerebral β-amyloid angiopathy, retinal ganglion cell degeneration in glaucoma, prion diseases, cataracts, tauopathies, frontotemporal lobar degeneration (FLTD), FTLD-FUS, amyotrophic lateral sclerosis (ALS/Lou Gehrig's disease), cerebral autosomal dominant arteriopathy with subcortical infarcts and leukoencephalopathy (CADASIL), Alexander disease, familial amyloidotic neuropathy, senile systemic amyloidosis, serinopthies, Cystic Fibrosis, and Sickle Cell Disease.

Provided herein is a method of treatment of a disease selected from the group above, the method comprising administering to a human in need thereof a pharmaceutically effective amount of a compound of Formula I, or a pharmaceutically acceptable salt thereof. Additional methods for treatment of these diseases comprise administration to the human in need thereof a compound of Formula II, Formula III, Formula IV, Formula V, Formula VI, Formula VII, or an individual compound herein, or a pharmaceutically acceptable salt thereof. The compound of this invention may be administered alone or in combination with other PARP inhibitors, such as small molecule inhibitors or antibodies. For all methods and uses described herein comprising the use of a compound of Formula I, or a pharmaceutically acceptable salt thereof, It is understood that comparable methods or uses are provided using, respectively, a compound of Formula II, Formula III, Formula IV, Formula V, Formula VI, Formula VII, and the individual compounds described herein, or a pharmaceutically acceptable salt thereof.

Additionally provided herein is the use of a compound of any of Formula I, Formula II, Formula III, Formula IV, Formula V, Formula VI, Formula VII, or a pharmaceutically acceptable salt thereof, in the preparation of a medicament. Additional embodiments comprise the use of a compound of any of Formula I, Formula II, Formula III, Formula IV, Formula V, Formula VI, Formula VII, or a pharmaceutically acceptable salt thereof, in the preparation of a medicament for treating each of the diseases or disorders described herein.

Provided herein is a method of sensitizing a cell, such as a cancer cell, to a DNA-damaging agent, the method comprising administering to a human in need thereof a pharmaceutically effective amount of a compound as described herein, or a pharmaceutically acceptable salt thereof.

Also provided is a method of treating a protein folding or a protein misfolding disease in a human, the method comprising administering to a human in need thereof a pharmaceutically effective amount of a compound of Formula I, or a pharmaceutically acceptable salt thereof.

DNA damaging agents will be known by those skilled in the art. Examples of chemotherapeutic DNA damaging agents include cisplatin, carboplatin, oxaliplatin, picoplatin, dicycloplatin, eptaplatin, lobaplatin, miriplatin, nedaplatin, satraplatin, triplatin tetranitrate, doxorubicin, daunorubicin, epirubicin, idarubicin, procarbazine, altretamine, radiotherapy and radiomimetics, such as bleomycin, monofunctional alkylators, including alkylsulphonates, nitrosorosourea compounds (carmustine, lomustine, streptozocin, and semustine), temozolomide, Antimetabolites (5-fluorouracil, capecitabine, floxuridine, gemcitabine, 6-mercaptopurine, 8-azaguanine, fludarabine, cladribine, methotrexate, aminopterin, and pemetrexed), thiopurines, and folate analogues and antifolates (ralitrexed), topoisomerase inhibitors such as camptothecins and etoposide, replication inhibitors such as aphidicoliin and hydroxyurea, calicheamicins and calicheamicin-derived antibody-drug conjugates (ADCs, such as Inotuzumab ozogamicin), and nitrogent mustards (cyclophosphamide, chlormethine, Melphalan, Chlorambucil, Ifosfamide, Bendamustine).

Provided herein is a method of enhancing the function of a DNA damaging agent in a human in need thereof, the method comprising administering to the human a pharmaceutically effective amount of a compound of Formula I, or a pharmaceutically acceptable salt thereof. Comparable methods of enhancing the function of a DNA damaging agent include the use, respectively, of a compound of Formula II, Formula III, Formula IV, Formula V, Formula VI, Formula VII, or any of the specific compounds described herein, or a pharmaceutically acceptable salt thereof. In one embodiment, the compound of this invention is administered simultaneously with the DNA damaging agent. In other embodiments, the compound of this invention is administered subsequently to the DNA damaging agent. For example, the compound of this invention may be administered at a time of 10 minutes, 20 minutes, 30 minutes, 45 minutes, 1 hour, 1 hour and a half, 2 hours, 2 and a half hours, 3 hours, 3 and a half hours, 4 hours, 4 and a half hours, 5 hours, 5 and a half hours, 6 hours, 6 and a half hours, 7 hours, 7 and a half hours, 8 hours, etc., following the administration of the DNA damaging agent. In other embodiments, the compound is administered prior to the DNA damaging agent, including at time periods of the lengths just listed for subsequent administration.

Also provided is a method of treating a subject, such as a human subject, with an ER stress-related condition, the method comprising administering to the human in need thereof a pharmaceutically effective amount of a compound of Formula I, or a pharmaceutically acceptable salt thereof. Separate embodiments also provide for the treatment of an ER stress-related condition in a human comprising, separately, administering to the human in need thereof a pharmaceutically effective amount of a compound Formula II, Formula III, Formula IV, Formula V, Formula VI, or Formula VII, or a pharmaceutically acceptable salt thereof.

Further provided is a method of regulating the unfolded protein response (UPR) of the endoplasmic reticulum (ER) in a human, the method comprising administering to a human in need thereof a pharmaceutically effective amount of a compound of Formula I, or a pharmaceutically acceptable salt thereof.

Also provided is the use of each compound described herein, or a pharmaceutically acceptable salt thereof, for use in each of the methods of treatment described herein. Further provided is the use of each compound described herein, or a pharmaceutically acceptable salt thereof, for use in preparation of a medicament for each of the methods and diseases or maladies described herein.

Compounds of Formula I, Formula II, Formula III, and Formula IV, Formula V, Formula VI, Formula VII, or a pharmaceutically acceptable salt or co-crystal thereof, are usually administered in the form of pharmaceutical compositions. This disclosure therefore provides pharmaceutical compositions that contain, as the active ingredient, one or more of the compounds described, or a pharmaceutically acceptable salt, pharmaceutically acceptable co-crystal or pharmaceutically acceptable ester thereof, and one or more pharmaceutically acceptable vehicle, such as excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed.

(1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the compound of Formula I (including those of Formulas II, III, IV, V, and VI), or a pharmaceutically acceptable salt or co-crystal thereof, may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline may also conventionally be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. In some embodiments, for parenteral administration, sterile injectable solutions are prepared containing a therapeutically effective amount, e.g., 0.1 to 1000 mg, of the compound of Formula I (including those of Formulas II, III, IV, V, VI, and VII), or a pharmaceutically acceptable salt or co-crystal thereof. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

Oral administration is another route for administration of the compound of Formula I (including those of Formulas II, III, IV, V, VI, and VII), or a pharmaceutically acceptable salt or co-crystal thereof. Administration may be via capsule or enteric-coated tablets, or the like. In making the pharmaceutical compositions that include the compound of Formula I (including those of Formulas II, III, IV, V, VI, and VII), or a pharmaceutically acceptable salt or co-crystal thereof, the active ingredient is usually diluted by an excipient and/or enclosed within such a carrier that can be in the form of a capsule, sachet, paper, or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients in an oral formulation include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical compositions as described herein can be formulated so as to provide quick, sustained, or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices (patches). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient is mixed with a pharmaceutical excipient to form a solid pre-formulation composition containing a homogeneous mixture of the compound of Formula I (including those of Formulas II, III, IV, V, VI, and VII), or a pharmaceutically acceptable salt or co-crystal thereof. When referring to these pre-formulation compositions as homogeneous, it is meant that the active ingredient is dispersed evenly throughout the composition so that the composition may be readily subdivided into equally effective unit dosage forms such as tablets, pills, and capsules.

The tablets or pills as described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

For any of the dosage units as described herein, it will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

The modifier "about" used in connection with a quantity is inclusive of the stated value and has the meaning dictated by the context (e.g., includes the degree of error associated with measurement of the particular quantity).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

Scheme 1 below represents a synthetic route to ITK1-4 (Examples 1-4), with reagents and conditions a) $H_2SO_4$, MEOH, 80° C.; b) chloracetonitrile, 4M HCl (1,4-dioxane), 110° C.; and c) NaH, DMF, RT.

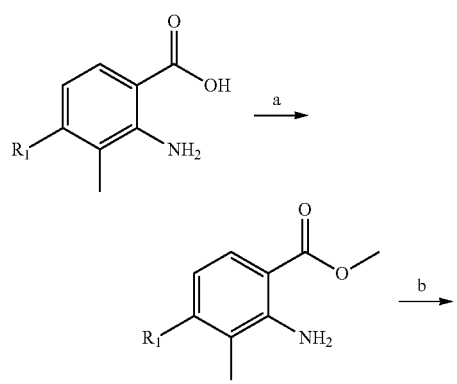

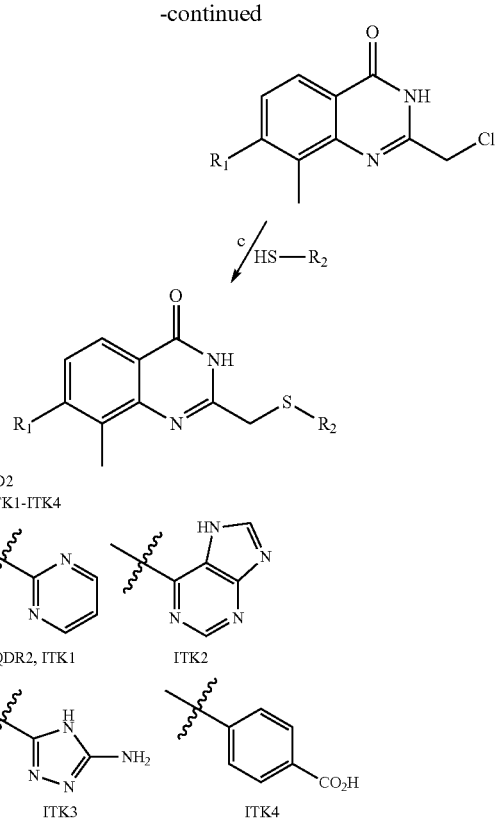

Scheme 2, below, provides a synthesis for ITK5-ITK7 (Examples 5 through 7).

Reagents and conditions: a) $(NH_2OH)_2 \cdot H_2SO_4$, HCl, $NaSO_4$, $H_2O$, 35-75° C.; b) $H_2SO_4$, 80° C.; c) $H_2O_2$ (30%), 1 M NaOH, then HCl, RT; d) cat. $H_2SO_4$, MeOH, 80° C.; e) ITK5: TMS-acetylene and $Pd(PPh_3)_2Cl_2$ (10% molar), ITK6 and ITK7: Tributyl(1-propynyl)tin and palladium tetrakis (10% molar), toluene, 115° C.; f) chloroacetonitrile, 4 M HCl (1,4-dioxane), 110° C.; g) NaH, DMF, RT.

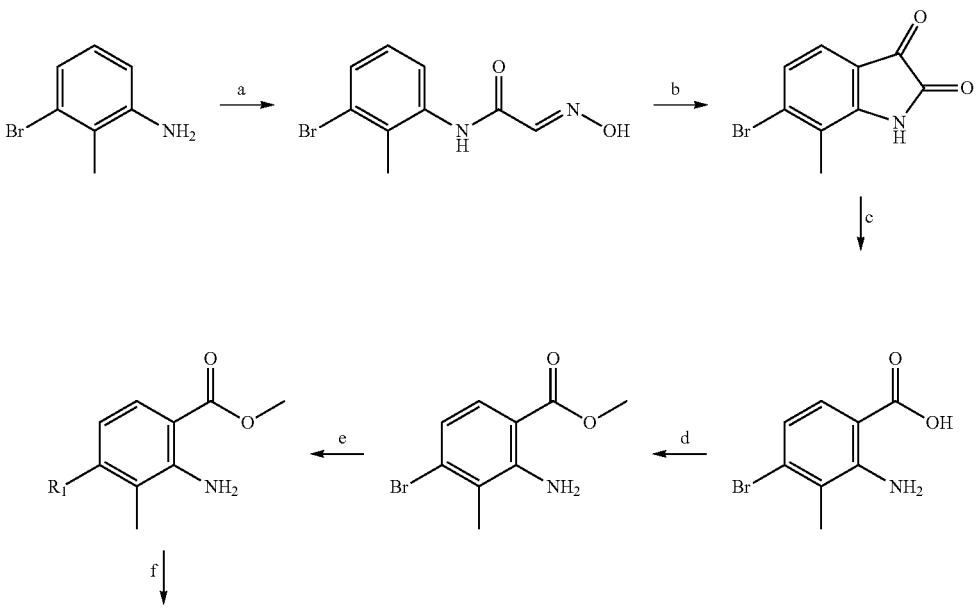

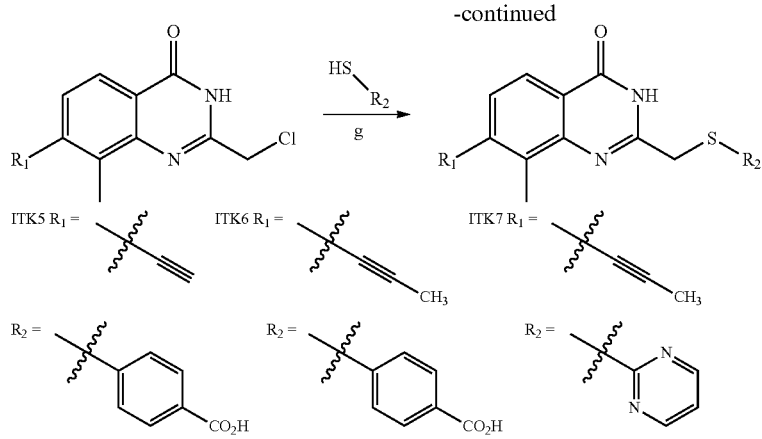

Chemical Synthesis

General: 1H NMR spectra were recorded on a Bruker DPX spectrometer at 400 MHz. Chemical shifts are reported as parts per million (ppm) downfield from an internal tetramethylsilane standard or solvent references. For air-and water sensitive reactions, glassware was flame- or oven-dried prior to use and reactions were performed under argon. Dimethylformamide was dried using the solvent purification system manufactured by Glass Contour, Inc. (Laguna Beach, CA). All other solvents were of ACS chemical grade (Fisher Scientific) and used without further purification unless otherwise indicated. Commercially available starting reagents were used without further purification. Analytical thin-layer chromatography was performed with silica gel 60 F254 glass plates (SiliCycle). Flash column chromatography was conducted self-packed columns containing 200-400 mesh silica gel (SiliCycle) on a Combiflash® Companion® purification system (Teledyne ISCO). High performance liquid chromatography (HPLC) was performed on a Varian Prostar 210 (Agilent) using Polaris 5 C18-A columns (Analytical: 150×4.6 mm, 3 μm; Preparative: 150×21.2 mm, 5 μm) (Agilent). All final products were ≥95% pure as assessed by analytical HPLC (mobile phase A: 0.1% formic acid (aq), mobile phase B: 0.1% formic acid in acetonitrile; flow rate=1.0 mL/min; conditions: pre-run A=% B=30%, 10 min A=5% B=95%, 12 min A=5% B=95%, 13 min A=70% B=30%; UV-Vis detection: λ1=254 nm, λ2=220 nm. Retention times (Rt) refer to UV=254 nm.

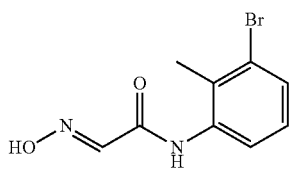

2-hydroxyimino-N-(2-methyl-3-bromo-phenyl)-acetamide: Trichloroacetylaldehyde hydrate (976 mg, 5.92 mmol) and anhydrous sodium sulfate (4.5 mg, 32 mmol) were dissolved in water (15 mL), and a suspension of 3-bromo-2-methyl-aniline (0.67 mL, 5.38 mmol) and hydroxylamine sulfate (4.4 g, 27 mmol) in 1 N HCl (6 mL) was added. The resultant suspension of white solids in clear solution was stirred at 35° C. for 1 h, then 52° C. for 1.5 h, and finally 75° C. for 1 h. The reaction mixture was cooled to RT and the product isolated as pale tan solids by vacuum filtration: 1.61 g (117% crude); 1H NMR (400 MHz, Chloroform-d) δ 8.23 (s, 1H), 7.88 (d, J=8.1 Hz, 1H), 7.83 (s, 1H), 7.61 (s, 1H), 7.41 (d, J=8.0 Hz, 1H), 7.10 (t, J=8.1 Hz, 1H), 2.39 (s, 3H).

6-bromo-7-methylindoline-2,3-dione: 2-hydroxyimino-N-(2-methyl-3-bromo-phenyl)-acetamide (1.61 g, 6.24 mmol) was added in small portions to 60° C. sulfuric acid and stirred at 80° C. for 1 h. The reaction mixture was cooled to RT and the product isolated as bright orange solids by vacuum filtration: 649 mg (50% crude); 1H NMR (400 MHz, DMSO-d6) δ 11.28 (s, 1H), 7.34 (d, J=8.0 Hz, 1H), 7.28 (d, J=8.0 Hz, 1H), 2.24 (s, 3H).

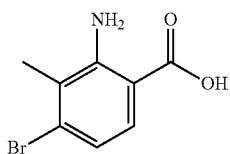

2-amino-4-bromo-3-methylbenzoic acid: 6-bromo-7-methylindoline-2,3-dione (649 mg, 2.70 mmol) dissolved in 1.3 N NaOH (135 mL) was combined with 30% $H_2O_2$ (7.0 mL) and water (70 mL) and stirred RT for 1 h. The reaction mixture was acidulated with 1 N HCl and the product precipitated as a white solid: 620 mg (99% crude, 45% over three steps); 1H NMR (400 MHz, DMSO-d6) δ 7.52 (d, J=8.6 Hz, 1H), 6.78 (d, J=8.7 Hz, 1H), 2.22 (s, 2H).

General procedure for synthesis of benzoates: To a solution of the appropriate benzoic acid in methanol was added concentrated sulfuric acid (1% v/v) at RT. The reaction mixture was refluxed at 90° C. for 18 h, monitored by TLC analysis (20% EtOAc in hexanes). Once complete the reaction mixture was poured over saturated aqueous sodium bicarbonate and separated with EtOAc. The aqueous layer was extracted with EtOAc (3×). The combined organic layers were washed with sat. aqueous sodium bicarbonate (1×), water (1×), and brine (1×), then dried over sodium sulfate and concentrated in vacuo to yield desired benzoate.

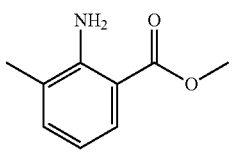

Methyl 2-amino-3-methylbenzoate: from 2-amino-3-methylbenzoic acid (500 mg, 3.3 mmol); yield 348 mg (64%); 1H NMR (400 MHz, Chloroform-d) δ 7.77 (ddd, J=8.1, 1.6, 0.6 Hz, 1H), 7.19 (ddq, J=7.2, 1.7, 0.8 Hz, 1H), 6.59 (dd, J=8.1, 7.2 Hz, 1H), 5.83 (s, 2H), 3.87 (s, 3H), 2.17 (d, J=0.7 Hz, 3H).

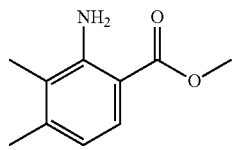

Methyl 2-amino-3,4-dimethylbenzoate: from 2-amino-3,4-dimethylbenzoic acid (500 mg, 3.0 mmol); yield 400 mg (75%); 1H NMR (400 MHz, Chloroform-d) δ 7.67 (d, J=8.2 Hz, 1H), 6.52 (d, J=8.3 Hz, 1H), 5.86 (s, 2H), 3.86 (s, 3H), 2.29 (s, 3H), 2.07 (s, 3H).

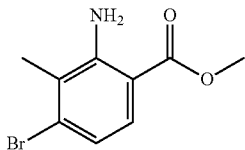

Methyl 2-amino-4-bromo-3-methylbenzoate: from 2-amino-4-bromo-3-methylbenzoic acid (620 mg, 2.69 mmol); yield 454 mg (69%); 1H NMR (400 MHz, DMSO-d6) δ 7.52 (dd, J=8.7, 4.5 Hz, 1H), 6.85 (s, 2H), 6.83-6.79 (m, 1H), 3.79 (d, J=1.4 Hz, 3H), 2.23 (d, J=5.4 Hz, 3H).

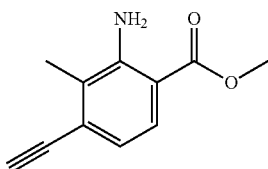

Methyl 2-amino-4-ethynyl-3-methylbenzoate: TMS-acetylene (0.85 mL, 6.15 mmol) and CuI (78 mg, 0.41 mmol) were dissolved in anhydrous DMF (2 mL) in an oven dried bomb flask (15 ml capacity) and stirred under argon at RT for 30 min; solution went from clear to orange. Pd(PPh3)2Cl2 (144 mg, 0.205 mmol), TEA (0.36 mL, 4.10 mmol), and Methyl 2-amino-4-bromo-3-methylbenzoate (500 mg, 2.05 mmol), and additional anhydrous DMF (10 mL) were quickly added, and the flask sealed under argon. The reaction proceeded at 110° C. for 18 h, solution turned black over several h. The flask was cooled to RT and the reaction mixture was diluted in EtOAc (20 mL) and filtered through celite. Organics were washed with water (100 mL, 3×), and brine (100 mL, 3×). The reaction was concentrated in vacuo and the residue purified on a Combiflash® Companion® system (4 g Redisep silica column; 0-10% EtOAc in hexanes). A mixture of the product (70%) and starting material (30%) was obtained as a yellow oil and taken on crude: 328 mg.1H NMR (400 MHz, DMSO d6) δ 7.53 (d, J=8.6 Hz, 1H), 6.85 (s, 2H), 6.81 (dd, J=8.7, 1.5 Hz, 1H), 3.79 (d, J=1.5 Hz, 3H), 2.23 (d, J=1.4 Hz, 3H).

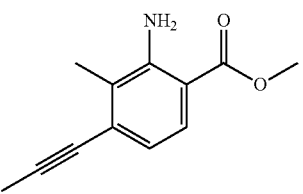

Methyl 2-amino-3-methyl-4-(prop-1-yn-1-yl)benzoate: methyl 2-amino-3-methyl-4-bromobenzoate (200 mg, 0.99 mmol) was dissolved in anhydrous toluene and concentrated (3×4 mL) then dried under vacuum for 1 h. The flask was evacuated and refilled with argon gas (3×), then anhydrous toluene (8 mL) was added via syringe and the solution degassed with argon 10 min. Tributyl(1-propynyl)tin (0.36 mL, 1.20 mmol) was added via syringe and the solution degassed 5 min. Palladium tetrakis (124 mg, 0.11 mmol) was added quickly and the solution degassed with argon for 3 min. The reaction mixture was refluxed at 115° C. for 2.5 h. TLC analysis (10% EtOAc in hexanes) showed consumption of starting benzoate. The reaction was cooled to RT and concentrated in vacou. The crude residue was purified via a Combiflash® Companion® system (4 g Redispe silica column; 0-20% EtOAc in hexanes). Product was isolated as a solid: 130 mg (80%); 1H NMR (400 MHz, Chloroform-d) δ 7.68 (d, J=8.3 Hz, 1H), 6.71 (d, J=8.4 Hz, 1H), 5.88 (s, 2H), 3.86 (s, 3H), 2.28 (s, 3H), 2.11 (s, 3H).

General procedure for synthesis of quinazolin-4(3H)-ones: The appropriate benzoate was added to a flame-dried flask and dissolved in 4 M HCl (1,4-dioxane) under argon. To this solution was added chloroacetonitrile (3 eqv.) and the reaction mixture was refluxed under argon at 125° C. overnight. Once TLC analysis revealed consumption of the starting benzoate the reaction was cooled to RT and poured over cold sat. aqueous sodium bicarbonate and left to stand at 4° C. The desired quinazolin-4(3H)-one readily precipitated and was collected by vacuum filtration.

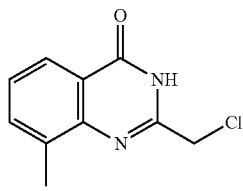

2-(chloromethyl)-8-methylquinazolin-4(3H)-one: from methyl 2-amino-3-methylbenzoate (250 mg, 1,52 mmol); yield 210 mg (48%); 1H NMR (400 MHz, DMSO-d6) δ 12.57 (s, 1H), 7.97 (d, J=7.9 Hz, 1H), 7.70 (d, J=7.5 Hz, 1H), 7.44 (t, J=7.6 Hz, 1H), 4.56 (d, J=1.3 Hz, 2H), 2.53 (d, J=9.2 Hz, 3H).

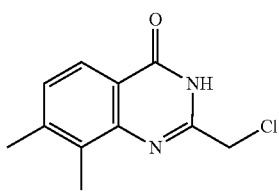

2-(chloromethyl)-7,8-dimethlyquinazolin-4(3H)-one): from methyl 2-amino-3,4-dimethylbenozate (400 mg, 2.23 mmol); yield 343 mg (69%); 1H NMR (400 MHz, Chloroform-d) δ 9.53 (s, 1H), 8.05 (d, J=8.1 Hz, 1H), 7.33 (d, J=8.1 Hz, 1H), 4.60 (s, 2H), 2.54 (s, 3H), 2.44 (s, 3H).

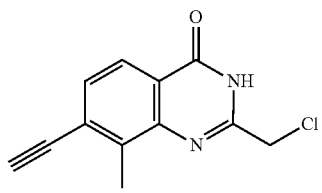 [SMILES: C#Cc1ccc2c(=O)[nH]c(CCl)nc2c1C]

2-(chloromethyl)-7-ethynyl-8-methylquinazolin-4(3H)-one: from methyl 2-amino-4-ethynyl-3-methylbenzoate (117 mg, 0.45 mmol); yield 80 mg (77%); 1H NMR (400 MHz, Chloroform-d) δ 10.48 (s, 1H), 8.10-8.05 (m, 1H), 7.55 (d, J=8.3 Hz, 1H), 4.61 (s, 2H), 2.71 (s, 3H), 0.30 (s, 9H).

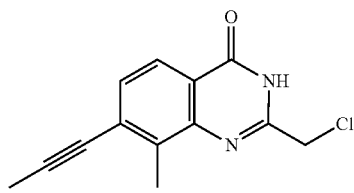 [SMILES: CC#Cc1ccc2c(=O)[nH]c(CCl)nc2c1C]

2-(chloromethyl)-8-methyl-7-(prop-1-yn-1-yl)quinazolin-4(3H)-one: from methyl 2-amino-3-methyl-4-(prop-1-yn-1-yl)benzoate (125 mg, 0.62 mmol); yield 115 mg (82%). 1H NMR (400 MHz, DMSO-d6) δ 12.64 (s, 1H), 7.90 (d, J=8.2 Hz, 1H), 7.47 (d, J=8.2 Hz, 1H), 4.56 (s, 2H), 2.62 (s, 3H), 2.16 (s, 3H).

General procedure for synthesis of ((pyrimidin-2-ylthio)methyl)quinazolin-4(3H)-ones: The appropriate thiol (2 eqv.) and sodium hydride (2 eqv.) were dissolved in anhydrous DMF and stirred at RT for 20 min. The appropriate quinazolin-4(3H)-one was added as a solid and the reaction mixture stirred at RT for 20 min. Once complete by TLC analysis (100% EtOAc) the reaction was poured over water, isolated, and purified as indicated.

QRD2

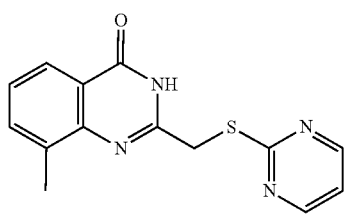

Example 1. 8-methyl-2-((pyrimidin-2-ylthio)methyl)quinazolin-4(3H)-one, QDR2: From 2-(chloromethyl)-8-methylquinazolin-4(3H)-one(112 mg, 0.54 mmol); reaction was concentrated in vacuo and product recovered as a white solid; yield 55.3 mg (36%); 1H NMR (400 MHz, DMSO-d6) δ 12.46 (s, 1H), 8.70 (d, J=4.9 Hz, 2H), 7.98-7.94 (m, 1H), 7.70-7.64 (m, 1H), 7.40 (t, J=7.6 Hz, 1H), 7.29 (t, J=4.9 Hz, 1H), 4.48 (s, 2H), 2.48 (s, 3H); Rt: 5.81 min. HRMS m/z [M+H]+ for C14H13N4OS: 285.08046, found 285.08128.

ITK1

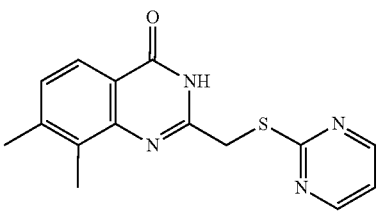

Example 2. 7,8-dimethyl-2-((pyrimidin-2-ylthio)methyl)quinazolin-4(3H)-one, ITK1: from 2-(chloromethyl)-7-methylquinazolin-4(3H)-one (18 mg, 0.08 mmol) and 2-mercaptopyrimidine; product precipitated as fine white solids in water; yield 15 mg (63%); 1H NMR (400 MHz, Chloroform-d) δ 10.96 (s, 1H), 8.68 (d, J=4.9 Hz, 2H), 8.01 (d, J=8.0 Hz, 1H), 7.17 (t, J=4.9 Hz, 1H), 4.33 (s, 2H), 2.56 (s, 3H), 2.43 (s, 3H); Rt: 7.58 min. HRMS m/z [M+H]+ for C15H16N4OS: 299.09611, found 299.09727.

ITK2

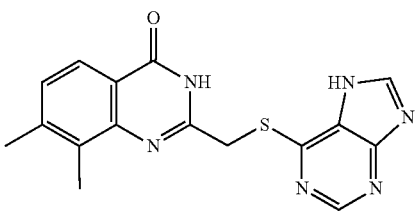

Example 3. 2-(((7H-purin-6-yl)thio)methyl)-7,8-dimethylquinazolin-4(3H)-one, ITK2: from 2-(chloromethyl)-7,8-dimethylquinazolin-4(3H)-one (25 mg, 0.11 mmol) and mercaptopurine; product precipitated as a white solid partition between water and EtOAc; yield 9.9 mg (27%); 1H NMR (400 MHz, DMSO-d6) δ 8.73 (s, 1H), 8.54 (s, 1H), 7.84 (d, J=8.0 Hz, 1H), 7.30 (d, J=7.7 Hz, 1H), 4.68 (s, 2H), 3.57 (d, J=1.8 Hz, 2H), 2.39 (s, 6H); Rt: 5.84 min. HRMS m/z [M−H]+ for C16H15N6OS: 337.08661, found 337.08676.

ITK3

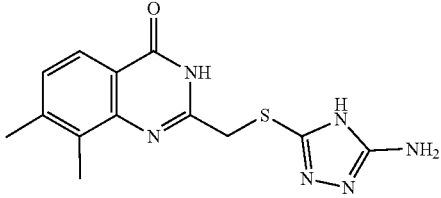

Example 4. 2-(((5-amino-4H-1,2,4-triazol-3-yl)thio)methyl)-7,8-dimethylquinazolin-4(3H)-one, ITK3: from 2-(chloromethyl)-7,8-dimethylquinazolin-4(3H)-one (25 mg, 0.11 mmol) and 3-Amino-5-mercapto-1,2,4-triazole; product precipitated as fine white solids in water; yield 25 mg (76%); 1H NMR (400 MHz, DMSO-d6) δ 12.28 (s, 1H), 12.09 (s, 1H), 7.84 (d, J=8.1 Hz, 1H), 7.31 (d, J=8.1 Hz, 1H), 6.20 (s, 2H), 4.19 (s, 2H), 2.44 (s, 3H), 2.38 (s, 3H;. Rt: 4.76 min. HRMS m/z [M−H]+ for C13H15N6OS: 301.08661, found 301.08712.

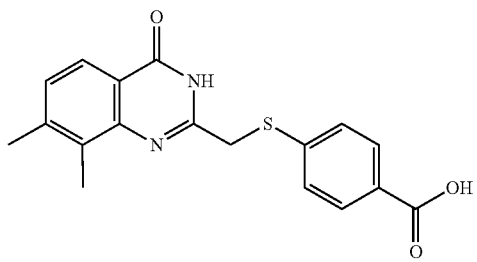

ITK4

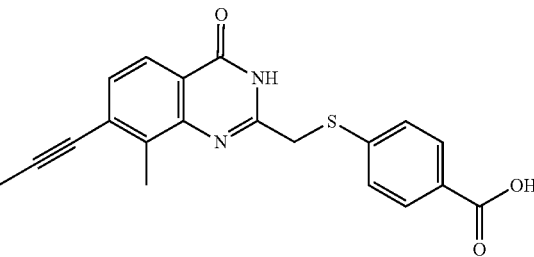

ITK6

Example 6. 4-(((8-methyl-4-oxo-7-(prop-1-yn-1-yl)-3,4-dihydroquinazolin-2-yl)methyl)thio) benzoic acid, ITK6: from 2-(chloromethyl)-8-methyl-7-(prop-1-yn-1-yl)quinazolin-4(3H)-one (90 mg, 0.39 mmol); product precipitated as a white solid in water; yield 80.2 mg (56%); ¹H NMR (400 MHz, DMSO-d6) δ 12.96 (s, 1H), 12.50 (s, 1H), 7.88-7.82 (m, 3H), 7.62 (d, J=8.3 Hz, 2H), 7.40 (d, J=8.2 Hz, 1H), 4.25 (s, 3H), 2.14 (s, 3H); Rt: 8.85 min. HRMS m/z [M+H]+ for C20H17N2O3S: 365.09544, found 365.09574.

Example 5. 4-(((7,8-dimethyl-4-oxo-3,4-dihydroquinazolin-2-yl)methyl)thio)benzoic acid, ITK4: from 2-(chloromethyl)-7,8-dimethylquinazolin-4(3H)-one (25 mg, 0.11 mmol) and 4-mercaptobenzoic acid; product precipitated as pale yellow solids in water; yield 27 mg (73%); 1H NMR (400 MHz, DMSO-d6) δ 12.95 (s, 1H), 12.33 (s, 1H), 7.93 (d, J=8.3 Hz, 1H), 7.83 (t, J=7.2 Hz, 2H), 7.63 (d, J=8.1 Hz, 2H), 7.29 (d, J=8.1 Hz, 1H), 4.26 (s, 2H), 2.41 (s, 3H), 2.36 (s, 3H); Rt: 6.70 min. HRMS m/z [M−H]+ for C18H16N2O3S: 339.07979, found 339.08030.

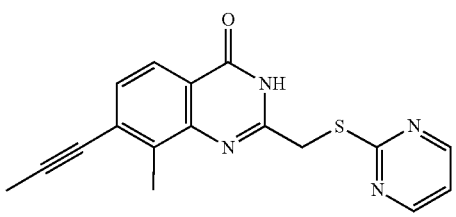

ITK7

Example 7. 8-methyl-7-(prop-1-yn-1-yl)-2-((pyrimidin-2-ylthio)methyl)quinazolin-4(3H)-one, ITK7: from 2-(chloromethyl)-8-methyl-7-(prop-1-yn-1-yl)quinazolin-4(3H)-one (15 mg, 0.06 mmol); reaction poured over water and extracted with EtOAc (3×), combined organic layers were washed with sat. aqueous sodium bicarbonate (2×), and brine (2×), then dried over sodium sulfate and concentrated in vacuo to give tan solids; yield 15.1 mg (76%); ¹H NMR (400 MHz, DMSO-d6) i5 12.49 (s, 1H), 8.66 (d, J=4.9 Hz, 2H), 7.87 (d, J=8.0 Hz, 1H), 7.41 (d, J=8.2 Hz, 1H), 7.25 (t, J=4.9 Hz, 1H), 4.44 (s, 2H), 2.53 (s, 3H), 2.14 (s, 3H). Rt: 8.90 min. HRMS m/z [M+Ht for C17H15N4O1S1: 323.09611, found 323.09656.

Crystallography Studies

Molecular Cloning, Protein Expression, and Purification

A synthetic cDNA fragment encoding a C-terminal segment of human PARP14 (Q460N5-6), codon optimized for expression in *Escherichia coli*, was obtained from GenScript. The fragment encoding Asp1611-Lys1801 was inserted into pNIC-NHD (GenBank: FN677494.1). The expression construct included an N-terminal affinity tag consisting of a hexahistidine sequence separated from the protein sequence by a TEV (tobacco etch virus) protease cleavage site (sequence: MHHHHHHSSGVDLGTEN-LYFQSM; SEQ ID NO: 1). *Escherichia coli* BL21 (DE3) R3 pRARE cells transformed with the expression construct were used to inoculate 3 l Terrific Broth medium supplemented with 8 g/L glycerol, 50 μg/mL kanamycin and Antifoam 204 (Sigma). Cultures were grown in Tune Air shake flasks at 37° C. When OD$_{600}$ of approximately 1.5 was

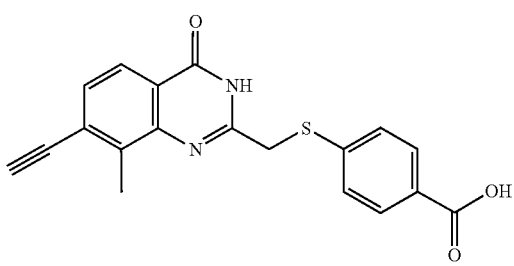

ITK5

Example 6. 4-(((7-ethynyl-8-methyl-4-oxo-3,4-dihydroquinazolin-2-yl)methyl)thio)benzoic acid, ITK5: from 2-(chloromethyl)-7-ethynyl-8-methylquinazolin-4(3H)-one (10 mg, 0.043 mmol); crude product precipitated as fine white solids in water then purified by HPLC (mobile phase A: water; mobile phase B: methanol; flow rate: 20 mL/min; conditions: pre-run A=5% B=95%, 7 min: A=5% B=95%, 10 min: A=5% B=95%, 11 min: A=35% B=65%, 15 min: A=35% B=95; Retention time: 4.29 min; UV-Vis detection: λ1 254 nm, λ2=220 nm. Yield 6.1 mg (42%); ¹H NMR (400 MHz, DMSO-d6) δ 12.55 (s, 1H), 7.89 (d, J=8.2 Hz, 1H), 7.85 (d, J=8.1 Hz, 2H), 7.62 (d, J=8.0 Hz, 2H), 7.49 (d, J=8.2 Hz, 1H), 4.70 (s, 1H), 4.26 (s, 2H), 2.56 (s, 3H); Rt: 8.21 min. HRMS m/z [M−H]+ for C19H14N2O3S: 349.06414, found 349.06489.

reached, the temperature was lowered to 18° C. and protein expression was induced by addition of 0.5 mM isopropyl β-D-thiogalactopyranoside and continued for approximately 20 h. Cells were harvested by centrifugation at 4430 g for 10 min in a Sorvall SLC-6000 rotor. The resulting pellet was suspended in 80 mL lysis buffer (100 mM Hepes, 500 mM NaCl, 10% glycerol, 10 mM Imidazole, 0.5 mM TCEP, pH 8.0) supplemented with 1 tablet of Complete EDTA-free Protease Inhibitor (Roche Biosciences) and 8 μL benzonase (2000 U). Suspended cells were stored at −80° C. The cells were thawed and sonicated on ice (Sonics VibraCell) at 80% amplitude, pulse: 4" on and 4" off, for a total time of 3 mins, followed by centrifugation at 49000×g in a Sorvall SA-800 rotor, 20 mins at 4° C. The soluble fraction was decanted and filtered through a 0.45 μm filter. Protein purification using immobilized metal affinity chromatography followed by size exclusion chromatography were carried out as previously described. Target protein mass was verified by mass spectrometry.

Protein Crystallization

Crystals of the PARP14-ITK1 complex were obtained by the sitting-drop vapor-diffusion method in a 96-well plate (Corning) by mixing 0.2 μl of protein at a concentration of 28 mg/ml including ITK1 dissolved in dimethyl sulfoxide (DMSO) and 0.2 μL of reservoir solution containing 20% poly(ethylene glycol) 3350, 0.2 M sodium nitrate. The plate was incubated at 20° C. After three weeks without any signs of crystal growth the plate was moved to 4° C. and small rod crystals appeared within five days. Crystals were quickly soaked in cryo solution supplemented with 20% glycerol, 300 mM sodium chloride and 0.2 mM ITK1 and then stored under liquid nitrogen.

Crystals of PARP14-ITK6 complex were obtained by mixing 0.1 μl of protein at a concentration of 30 mg/ml including ITK6 dissolved in dimethyl sulfoxide (DMSO) and 0.2 μl of reservoir solution containing 20% Poly(ethylene glycol) 3350, 0.2 M sodium nitrate and 0.1 M Bis-Tris-Propane pH 6.5. The plate was incubated at 4° C. Plate-shaped crystals appeared within seven weeks. Crystals were briefly soaked in cryo solution supplemented with 20% Glycerol, 200 mM sodium chloride and 4 mM ITK6 and then stored under liquid nitrogen.

Crystallographic Data Collection, Phasing, and Refinement

A data set extending to 2.15 Å resolution was collected on a PARP14-ITK1 crystal at 0.92819 Å wavelength on a Dectris Pilatus 6 M detector at beamline i04-1 at the Diamond Light Source (Oxfordshire, UK). The data were integrated and scaled using xia2. The crystal belonged to space group P1, and the Matthew's coefficient suggested the presence of four monomers in the asymmetric unit. The structure was solved using molecular replacement using Phaser and a previous structure of human PARP14 (PDB entry: 4F1L) as search model. Density for the ligand was observed in all chains and manual model building was done using COOT. Structure refinement was done using data in the interval 30.92-2.15 Å resolution with Buster and the progress of refinement was followed by decreasing R and Rfree values. Grade was used to obtain ligand restraints.

A data set extending to 2.67 Å resolution was collected on the best PARP14-ITK6 crystal at 0.96858 Å wavelength on a Dectris Pilatus 6 M detector at beamline i24 at Diamond Light Source (Oxfordshire, UK). The data were integrated and scaled using XDSAPP. The crystal belonged to space group P6122, and the Matthew's coefficient suggested the presence of two monomers in the asymmetric unit. The structure was solved using molecular replacement using Phaser and the PARP14·ITK1 structure as search model. Density for the ligand was observed in both chains and manual model building was done using COOT. Structure refinement was done using Buster. In the refinement, data in the interval 49.76-2.67 Å resolution was used and the progress of refinement was followed by decreasing R and Rfree values. Grade was used to obtain ligand restraints.

Tables 1a and 1b: In vitro $IC_{50}$ (μM) values for ITK1-6; SEM from a minimum of three dose-response experiments.

TABLE 1a

| QDR Analog | PARP 1 | PARP 2 | PARP 3 | PARP4 Brct-cat | PARP5 bcat | PARP10 cat | PARP11 | PARP14 cat-wwe | PARP15 cat |
|---|---|---|---|---|---|---|---|---|---|
| ITK1 | >30 | 17.4 ± 3.3 | >30 | nt | >10 | 19.7 ± 0.95 | 0.55 ± 0.11 | 8.55 ± 0.80 | >30 |
| ITK2 | >30 | >30 | >30 | nt | >10 | 32.8 ± 3.6 | 4.52 ± 1.4 | 7.87 ± 0.20 | >30 |
| ITK3 | >30 | >30 | >30 | nt | >10 | 27.9 ± 3.9 | 13.6 ± 1.4 | 6.73 ± 1.8 | >30 |
| ITK4 | >30 | 8.46 ± 1.40 | >30 | nt | >10 | 9.29 ± 0.20 | 5.50 ± 0.80 | 8.71 ± 0.80 | 6.85 ± 0.99 |
| ITK5 | >30 | >30 | >30 | nt | >10 | 5.40 ± 0.17 | 1.62 ± 0.33 | 10.8 ± 0.75 | 4.03 ± 0.77 |
| ITK6 | >30 | >30 | >30 | >30 | >30 | 0.156 ± 0.018 | 0.099 ± 0.016 | 0.917 ± 0.086 | 0.496 ± 0.19 | nt = not tested

TABLE 1b

| QDR Analog | PARP 6 | PARP 7 | PARP 8 | PARP 12 | PARP 16 |
|---|---|---|---|---|---|
| ITK1, ITK2, ITK3, ITK4, and ITK5 | nt | nt | nt | nt | nt |
| ITK6 | >3 | 24.6 ± 0.5 | >3 | nt | nt | nt = not tested

TABLE 2

In vitro IC50 values for olaparib, rucaparib, and ITK7; IC50 (μM) shown with SEM from a minimum of three dose response experiments.

| QDR Analoque | Olaparib | Rucaparib | ITK7 |
|---|---|---|---|
| PARP 1 | 0.025 ± 0.002 | 0.008 ± 0.002 | >30 |
| PARP 2 | 0.007 ± 0.0003 | 0.005 ± 0.001 | >30 |
| PARP 3 | 0.083 ± 0.037 | 0.72 ± 0.37 | >30 |
| PARP4 Brct-cat | 0.241 ± 0.015 | 0.450 ± 0.10 | >30 |
| PARP5 bcat | 0.211 ± 0.081 | 3.6 ± 0.3 | >30 |
| PARP6 | nt | nt | >3 |
| PARP7 | nt | nt | 2.46 ± 0.5 |
| PARP8 | >3 | >3 | >3 |
| PARP10cat | 4.5 ± 0.3 | 2.5 ± 0.2 | 9.28 ± 1.57 |
| PARP11 | >10 | 3.4 ± 0.5 | 0.014 ± 0.003 |
| PARP12 | ~10 | ~7 | >3 |
| PARP14 cat-wwe | >10 | >10 | 2.86 ± 0.35 |
| PARP15 cat | >10 | >10 | >30 |
| PARP16 | ~5 | n.i. | >3 | nt = not tested;
n.i. = no inhibition

For FIG. 1, recombinant PARPs were used in this study. Protein samples were run on a 4-20% gradient SDS-PAGE gel (Bio-Rad) and imaged for Coomassie staining on a ChemiDoc MP system (Bio-Rad).

Figure 2:
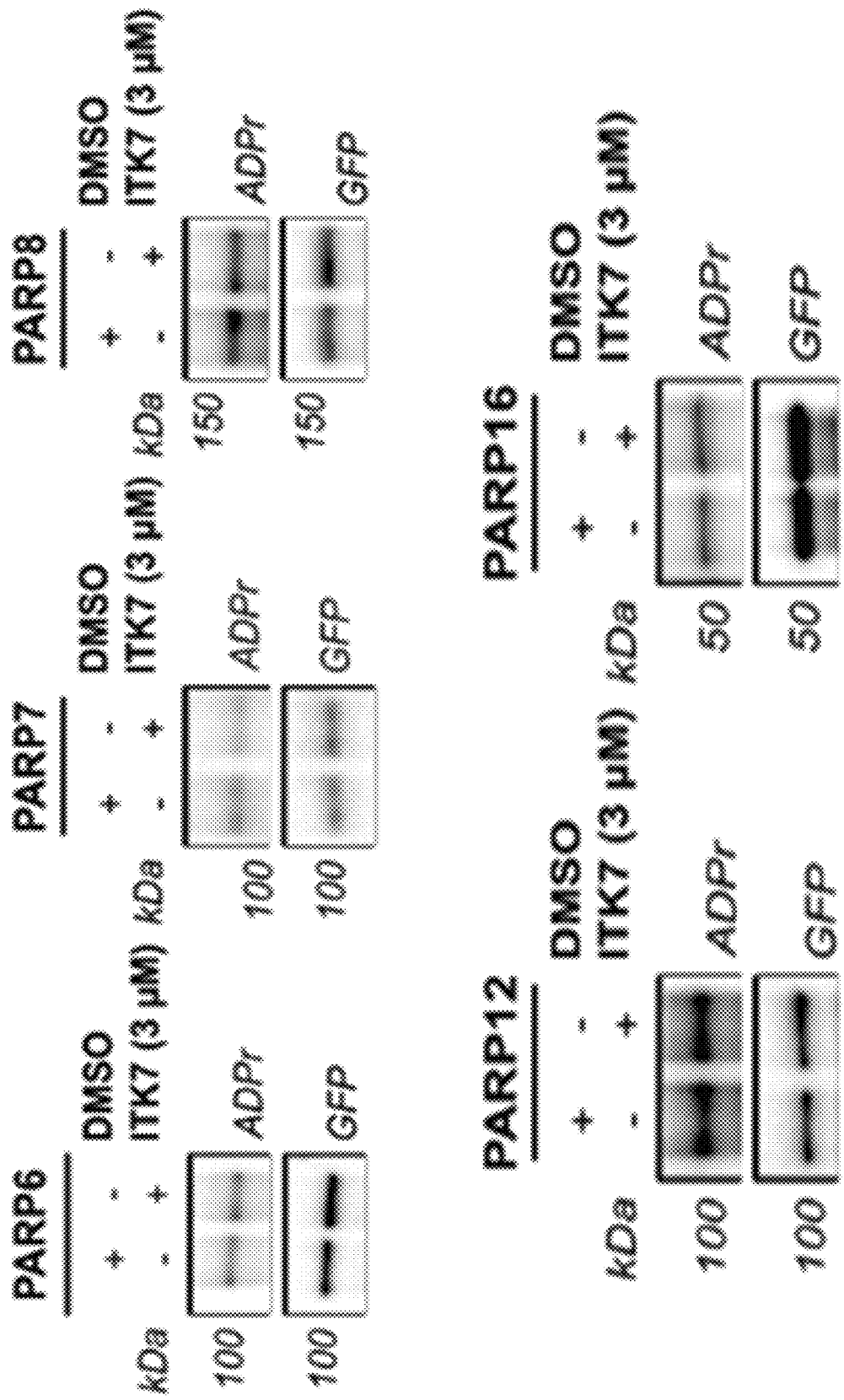
FIG. 2 represents Western blot analysis of immunoprecipitated PARPs incubated with DMSO or ITK7 (Example 7).

FIG. 2 represents HEK 293T cells transfected with GFP-PARP6, GFP-PARP8, GFP-PARP12, or GFP-PARP16 were lysed after 24 h and GFP-PARPs immunoprecipitated on magnetic beads. Immunoprecipitated PARPs were incubated with either DMSO or ITK7 (3 µM) for 1.5 h at 25° C. with 100 µM (GFP-PARP6-12) or 400 µM (GFP-PARP16) 6-a-NAD+ based on the literature Km of NAD+ (Thorsell et al., Med Chem. 60(4):1262-1271, 2017). Auto-MARylation was analyzed by Western blot with an ADP-ribose (ADPr) binding reagent (uncropped blots shown below).

Figure 3:
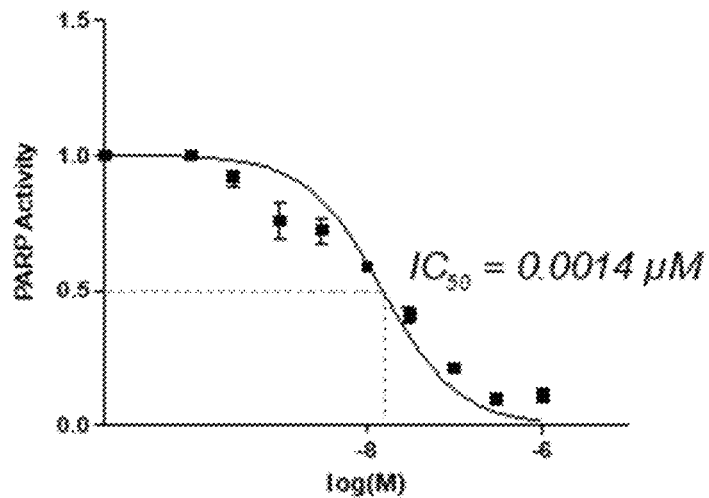
FIG. 3 provides dose response curves for ITK7 (Example 7) inhibiting PARP11 mediated MARylation of SRPK2 and NXF1 using either 6-a-NAD$^+$ or native NAD+ in in vitro plate assays.
Figure 3:
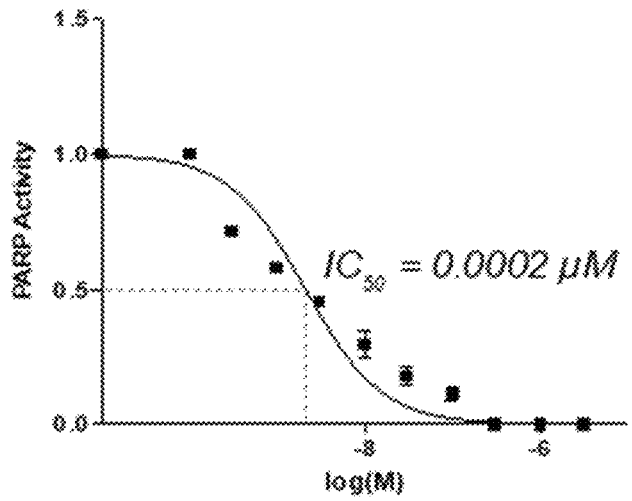
Figure 3:
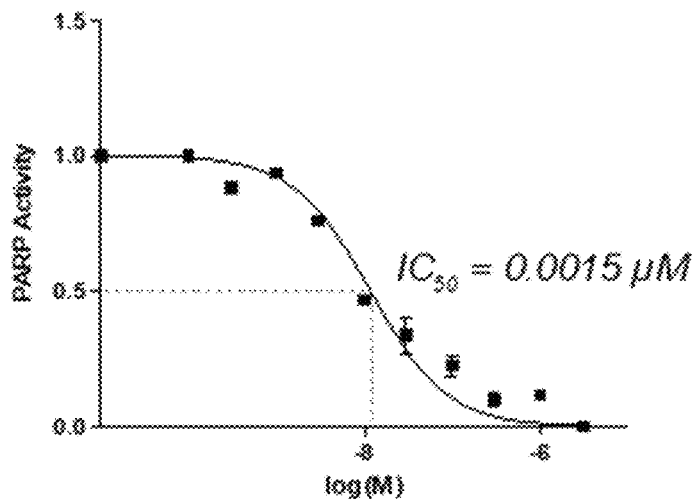

FIG. 3 depicts dose response curves for ITK7 inhibiting PARP11 mediated MARylation of SRPK2 and NXF1 using either 6-a-NAD+ or native NAD+ in in vitro plate assays. Curves generated using Prism 7 (Graph Pad); error bars indicate ±SEM from at least two replicates.

Figure 4A:
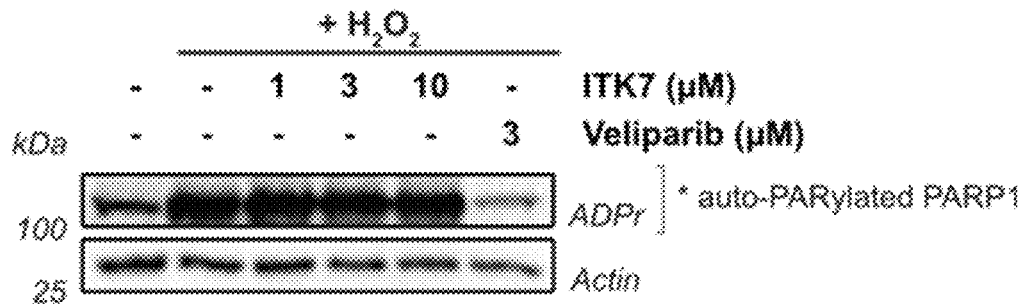
FIG. 4A provides a comparison of the lack of inhibition of H2O2-stimulated PARP1/2 activity versus veliparib.
Figure 4B:
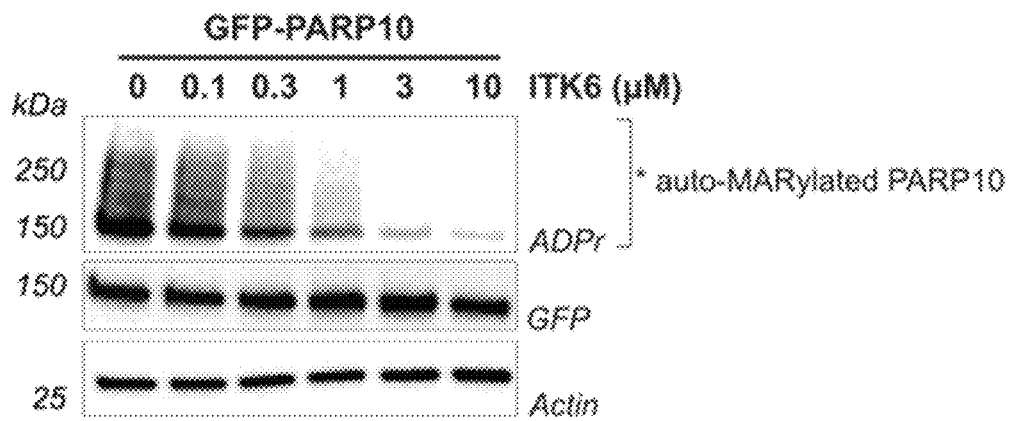
FIG. 4B demonstrates the PARP10 auto-MARylation inhibition accomplished by ITK6 (Example 6).
Figure 4C:
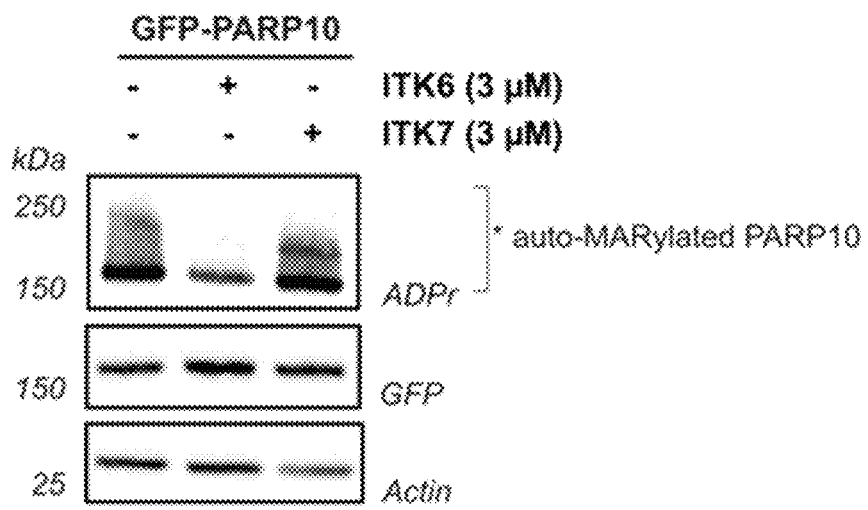
FIG. 4C demonstrates the inhibition of PARP 10 auto-MARylation by ITK6, but not ITK7.

FIGS. 4A, 4B, and 4C demonstrate that ITK7 (Example 7) does not inhibit PARP½ or PARP10 in cells. (FIG. 4A) ITK7 does not inhibit $H_2O_2$-stimulated PARP½ activity in cells. HEK 293T cells were stimulated with H2O2 (500 µM) for 15 min in the presence of DMSO, ITK7 or veliparib. As expected, veliparib, a PARP½-selective inhibitor, completely inhibits H2O2-mediated PARP1 PARylation while ITK7 has no effect. Lysates were prepared and PAR/MARylation was analyzed by Western blot with an ADP-ribose (ADPr) binding reagent. Blot was also probed with antibodies for GFP and actin. The band of interest represents auto-PARylated GFP-PARP1. (FIG. 4B) ITK6, a pan-H-Y-Φ PARP inhibitor, inhibits PARP10 auto-MARylation in cells in a dose dependent manner. HEK 293T cells were transfected with GFP-PARP10. Cells were then incubated with increasing concentrations of ITK6 for 90 min. Lysates were prepared and MARylation of PARP10 was analyzed by Western blot with an ADP-ribose (ADPr) binding reagent. Blot was also probed with antibodies for GFP and actin. (FIG. 4C) ITK6 inhibits PARP10 auto-MARylation in cells whereas ITK7 does not inhibit PARP10. HEK 293T cells were transfected with GFP-PARP10. 24 h post-transfection cells were treated with either ITK6 (3 µM) or ITK7 (3 µM) for 3 h. Lysates were prepared and PAR/MARylation was analyzed by Western blot with an ADP-ribose (ADPr) binding reagent. Blot was also probed with antibodies for GFP and actin.

Figure 5A:
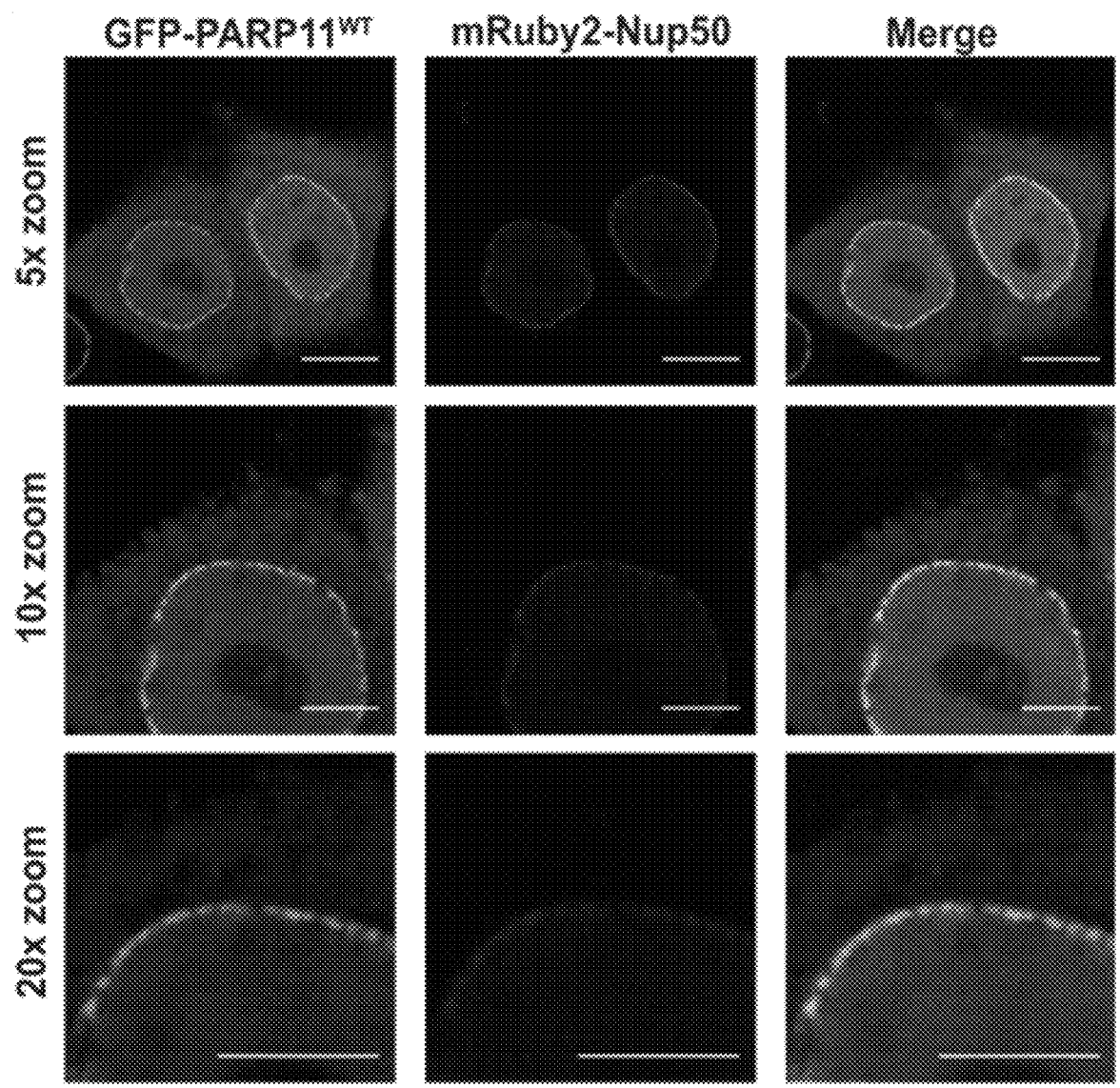
FIG. 5A depicts GFP-PARP11 and mRuby2-Nup50 co-localization at the nuclear envelope in HeLa cells.
Figure 5B:
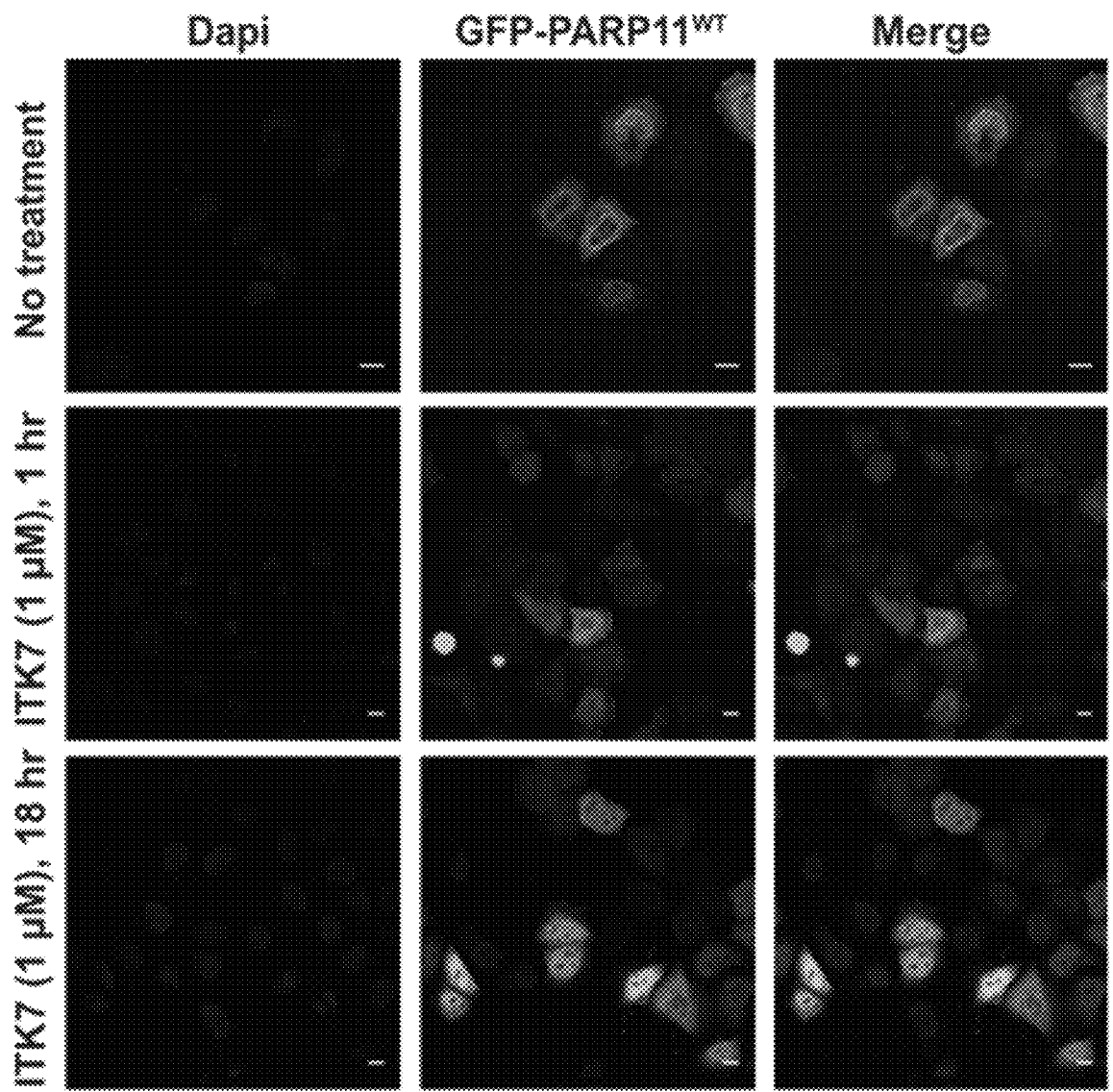
FIG. 5B depicts ITK7 treatment causing PARP11 disassociation from the nuclear envelope in HeLa cells.

FIGS. 5A and 5B depict dissociation from the nuclear envelope in HeLa cells following ITK7 (Example 7) treatment. ITK7 causes GFP-PARP11 to dissociate from the nuclear envelope. HeLa cells were transfected with GFP-PARP11 grown on glass cover-slips. After ITK7 (1 µM) treatment for 1 or 18 h cells were fixed and mounted using mounting medium containing DAPI. Images were taken on the Olympus FLUOVIEW™ 2000 microscope using an 60x/NA 1.40 oil objective (scale bar 10 µm).

GFP-PARP11 Co-Localizes With the Nuclear Pore Complex (NPC) Protein NUP50 and ITK7 Treatment Causes PARP11 to Dissociate From the Nuclear Envelope (FIG. 5A) GFP-PARP11 and mRuby2-Nup50 co-localize at the nuclear envelope. GFP-PARP11 and mRuby2-Nup50 were transfected in HeLa cells. Cells were grown in 8 well Lab-Tek with glass bottom. Images were taken sequentially to avoid any possible bleed through from GFP to the red channel. Images were acquired with 60x/NA 1.40 oil objective on Olympus FLUOVIEW™ 2000 microscope, with 5×, 10× or 20× zoom (Scale bar 10 µm in 5× zoom, and 5 µm in 10× and 20× zoom).

(FIG. 5B) ITK7 causes GFP-PARP11 to dissociate from the nuclear envelope. HeLa cells were transfected with GFP-PARP11 grown on glass cover-slips. After ITK7 (1 µM) treatment for 1 or 18 h cells were fixed and mounted using mounting medium containing DAPI. Images were taken on the Olympus FLUOVIEW™ 2000 microscope using an 60x/NA 1.40 oil objective (scale bar 10 µm).

ITK7 does not inhibit $H_2O_2$-stimulated PARP½ activity in cells. HEK 293T cells were stimulated with $H_2O_2$ (500 µM) for 15 min in the presence of DMSO, ITK7 or veliparib. As expected, veliparib, a PARP½-selective inhibitor, completely inhibits $H_2O_2$-mediated PARP1 PARylation while ITK7 has no effect. Lysates were prepared and PAR/MARylation was analyzed by Western blot with an ADP-ribose (ADPr) binding reagent. Blot was also probed with antibodies for GFP and actin. The band of interest represents auto-PARylated GFP-PARP1.

ITK6, a pan-H-Y-Φ PARP inhibitor, inhibits PARP10 auto-MARylation in cells in a dose dependent manner. HEK 293T cells were transfected with GFP-PARP10. Cells were then incubated with increasing concentrations of ITK6 for 90 min. Lysates were prepared and MARylation of PARP10 was analyzed by Western.

ITK6 inhibits PARP10 auto-MARylation in cells whereas ITK7 does not inhibit PARP10. HEK 293T cells were transfected with GFP-PARP10. 24 h post-transfection cells were treated with either ITK6 (3 µM) or ITK7 (3 µM) for 3 h. Lysates were prepared and PAR/MARylation was analyzed by Western blot with an ADP-ribose (ADPr) binding reagent.

What is claimed:

1. A compound of Formula I, or a pharmaceutically acceptable salt thereof:

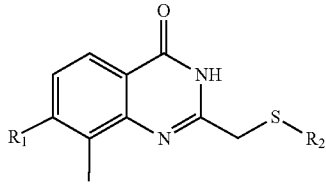

Formula I wherein
- $R_1$ is selected from the group consisting of $C_1$-$C_2$ alkyl, $C_2$-$C_3$ alkenyl, and $C_2$-$C_3$ alkynyl; and
- $R_2$ is selected from the group consisting of a phenyl ring and a 3-membered to 10-membered aromatic, partially unsaturated, or unsaturated heterocycle containing 1, 2, 3, or 4 ring nitrogen atoms, wherein the phenyl ring and the 5-membered to 10-membered aromatic, partially unsaturated, or unsaturated heterocycle being substituted by 0, 1, 2, or 3 substituents selected from the group consisting of Cl, F, Br, I, OH, $C_1$-$C_6$ alkyl, —O—$C_1$-$C_6$ alkyl, —$NH_2$, —NH($C_1$-$C_6$ alkyl), —N($C_1$-$C_6$ alkyl)$_2$, —$CO_2H$, —$CO_2$($C_1$-$C_6$ alkyl), —$CO_2$-phenyl, and —$CO_2$-benzyl; and wherein the phenyl and benzyl rings of the $R_2$, —$CO_2$-phenyl, and —$CO_2$-benzyl groups are substituted by 0, 1, 2, or 3 substituents selected from the group consisting of Cl, F, Br, I, OH, $C_1$-$C_6$ alkyl, —O—$C_1$-$C_6$ alkyl, —$NH_2$, —NH($C_1$-$C_6$ alkyl), and —N($C_1$-$C_6$ alkyl)$_2$.

2. The compound of claim 1, or a pharmaceutically acceptable salt thereof, wherein
- $R_1$ is selected from the group consisting of $CH_3$, $C_2$-$C_3$ alkenyl, and $C_2$-$C_3$ alkynyl; and
- $R_2$ is as defined in claim 1.

3. The compound of claim 1, or a pharmaceutically acceptable salt thereof, wherein
- $R_1$ is selected from the group consisting of $CH_3$, —CH=CH2, and $C_2$-$C_3$ alkynyl; and
- $R_2$ is as defined in claim 1.

4. The compound of claim 1, or a pharmaceutically acceptable salt thereof,
wherein
- $R_1$ is selected from the group consisting of $CH_3$, —CH=$CH_2$, and —C≡C—$CH_3$; and
- $R_2$ is as defined in claim 1.

5. The compound of claim 1, or a pharmaceutically acceptable salt thereof,
wherein
- $R_1$ is —C≡C—$CH_3$; and
- $R_2$ is as defined in claim 1.

6. The compound of claim 1, or a pharmaceutically acceptable salt thereof,
wherein
- $R_1$ is selected from the group consisting of $CH_3$, $C_2$-$C_3$ alkenyl, and $C_2$-$C_3$ alkynyl; and
- $R_2$ is selected from the group consisting of a phenyl ring and a 4-membered to 7-membered aromatic, partially unsaturated, or unsaturated heterocycle containing 1, 2, 3, or 4 ring nitrogen atoms, wherein the phenyl ring and the 4-membered to 7-membered aromatic, partially unsaturated, or unsaturated heterocycle being substituted by 0, 1, 2, or 3 substituents selected from the group consisting of Cl, F, Br, I, OH, $C_1$-$C_6$ alkyl, —O—$C_1$-$C_6$ alkyl, —$NH_2$, —NH($C_1$-$C_6$ alkyl), —N($C_1$-$C_6$ alkyl)$_2$, —$CO_2H$, —$CO_2$($C_1$-$C_6$ alkyl), —$CO_2$-phenyl, and —$CO_2$-benzyl; and wherein the phenyl and benzyl rings of the $R_2$, —$CO_2$-phenyl, and —$CO_2$-benzyl groups are substituted by 0, 1, 2, or 3 substituents selected from the group consisting of Cl, F, Br, I, OH, $C_1$-$C_6$ alkyl, —O—$C_1$-$C_6$ alkyl, —$NH_2$, —NH($C_1$-$C_6$ alkyl), and —N($C_1$-$C_6$ alkyl)$_2$.

7. The compound of claim 1, or a pharmaceutically acceptable salt thereof, wherein
- $R_1$ is selected from the group consisting of $CH_3$, —CH=CH2, and $C_2$-$C_3$ alkynyl; and
- $R_2$ is selected from the group consisting of a phenyl ring or a 4-membered to 6-membered aromatic, partially unsaturated, or unsaturated heterocycle containing 1, 2, 3, or 4 ring nitrogen atoms, wherein the phenyl ring and the 4-membered to 6-membered aromatic, partially unsaturated, or unsaturated heterocycle being substituted by 0, 1, 2, or 3 substituents selected from the group consisting of Cl, F, Br, I, OH, $C_1$-$C_6$ alkyl, —O—$C_1$-$C_6$ alkyl, —$NH_2$, —NH($C_1$-$C_6$ alkyl), —N($C_1$-$C_6$ alkyl)$_2$, —$CO_2H$, —$CO_2$($C_1$-$C_6$ alkyl), —$CO_2$-phenyl, and —$CO_2$-benzyl; and wherein the phenyl and benzyl rings of the $R_2$, —$CO_2$-phenyl, and —$CO_2$-benzyl groups are substituted by 0, 1, 2, or 3 substituents selected from the group consisting of Cl, F, Br, I, OH, $C_1$-$C_6$ alkyl, —O-$C_1$-$C_6$ alkyl, —$NH_2$, —NH($C_1$-$C_6$ alkyl), and —N($C_1$-$C_6$ alkyl)$_2$.

8. The compound of claim 1, or a pharmaceutically acceptable salt thereof, wherein
- $R_1$ is selected from the group consisting of $CH_3$, —CH=$CH_2$, and —C≡C—$CH_3$; and
- $R_2$ is a phenyl or 5-membered to 6-membered aromatic, partially unsaturated, or unsaturated heterocycle containing 1, 2, 3, or 4 ring nitrogen atoms, wherein the phenyl ring and the 5- to 6-membered aromatic, partially unsaturated, or unsaturated heterocycle being substituted by 0, 1, 2 or 3 substituents selected from the group consisting of Cl, F, Br, I, OH, $C_1$-$C_6$ alkyl, —O-$C_1$-$C_6$ alkyl, —$NH_2$, —NH($C_1$-$C_6$ alkyl), —N($C_1$-$C_6$ alkyl)$_2$, —$CO_2H$, —$CO_2$($C_1$-$C_6$ alkyl), —$CO_2$-phenyl, and —$CO_2$-benzyl; and wherein the phenyl and benzyl rings of the $R_2$, —$CO_2$-phenyl, and —$CO_2$-benzyl groups are substituted by 0, 1, 2, or 3 substituents selected from the group consisting of Cl, F, Br, I, OH, $C_1$-$C_6$ alkyl, —O-$C_1$-$C_6$ alkyl, —$NH_2$, —NH($C_1$-$C_6$ alkyl), and —N($C_1$-$C_6$ alkyl)$_2$.

9. The compound of claim 1, or a pharmaceutically acceptable salt thereof, wherein
- $R_1$ is —C≡C—$CH_3$; and
- $R_2$ is a 6-membered aromatic, partially unsaturated, or unsaturated heterocycle containing 1, 2, 3, or 4 ring nitrogen atoms, wherein the 6-membered aromatic, partially unsaturated, or unsaturated heterocycle being substituted by 0, 1, 2, or 3 substituents selected from the group consisting of Cl, F, Br, I, OH, $C_1$-$C_6$ alkyl, —O-$C_1$-$C_6$ alkyl, —$NH_2$, —NH($C_1$-$C_6$ alkyl), —N($C_1$-$C_6$ alkyl)$_2$, —$CO_2H$, —$CO_2$($C_1$-$C_6$ alkyl), —$CO_2$-phenyl, and —$CO_2$-benzyl; and wherein the phenyl and benzyl rings of the $R_2$, —$CO_2$-phenyl, and —$CO_2$-benzyl groups are substituted by 0, 1, 2, or 3 substituents selected from the group consisting of Cl, F, Br, I, OH, $C_1$-$C_6$ alkyl, —O-$C_1$-$C_6$ alkyl, —$NH_2$, —NH($C_1$-$C_6$ alkyl), and —N($C_1$-$C_6$ alkyl)$_2$.

10. The compound of claim 1, or a pharmaceutically acceptable salt thereof, wherein
R$_1$ is —C≡C—CH$_3$; and
R$_2$ is a 6-membered aromatic, partially unsaturated, or unsaturated heterocycle containing 1, 2, or 3 ring nitrogen atoms, wherein the 6-membered aromatic, partially unsaturated, or unsaturated heterocycle being substituted by 0, 1, 2, or 3 substituents selected from the group consisting of Cl, F, Br, I, OH, C$_1$-C$_6$ alkyl, —O-C$_1$-C$_6$ alkyl, —NH$_2$, —NH(C$_1$-C$_6$ alkyl), —N(C$_1$-C$_6$ alkyl)$_2$, —CO$_2$H, —CO$_2$(C$_1$-C$_6$ alkyl), —CO$_2$-phenyl, and —CO$_2$-benzyl; and wherein the phenyl and benzyl rings of the R$_2$, —CO$_2$-phenyl, and —CO$_2$-benzyl groups are substituted by 0, 1, 2, or 3 substituents selected from the group consisting of Cl, F, Br, I, OH, C$_1$-C$_6$ alkyl, —O-C$_1$-C$_6$ alkyl, —NH$_2$, —NH(C$_1$-C$_6$ alkyl), and —N(C$_1$-C$_6$ alkyl)$_2$.

11. The compound of claim 1, or a pharmaceutically acceptable salt thereof, wherein
R$_1$ is —C≡C—CH$_3$; and
R$_2$ is a 6-membered aromatic, partially unsaturated, or unsaturated heterocycle containing 1 or 2 ring nitrogen atoms, wherein the 6-membered aromatic, partially unsaturated, or unsaturated heterocycle being substituted by 0, 1, 2, or 3 substituents selected from the group consisting of Cl, F, Br, I, OH, C$_1$-C$_6$ alkyl, —O-C$_1$-C$_6$ alkyl, —NH$_2$, —NH(C$_1$-C$_6$ alkyl), —N(C$_1$-C$_6$ alkyl)$_2$, —CO$_2$H, —CO$_2$(C$_1$-C$_6$ alkyl), —CO$_2$-phenyl, and —CO$_2$-benzyl; and wherein the phenyl and benzyl rings of the R$_2$, —CO$_2$-phenyl, and —CO$_2$-benzyl groups are substituted by 0, 1, 2, or 3 substituents selected from the group consisting of Cl, F, Br, I, OH, C$_1$-C$_6$ alkyl, —O-C$_1$-C$_6$ alkyl, —NH$_2$, —NH(C$_1$-C$_6$ alkyl), and —N(C$_1$-C$_6$ alkyl)$_2$.

12. The compound of claim 1, or a pharmaceutically acceptable salt thereof, wherein
R$_1$ is —C≡C—CH$_3$; and
R$_2$ is a 6-membered aromatic, partially unsaturated, or unsaturated heterocycle containing 2 ring nitrogen atoms, wherein the 6-membered aromatic, partially unsaturated, or unsaturated heterocycle being substituted by 0, 1, 2, or 3 substituents selected from the group consisting of Cl, F, Br, I, OH, C$_1$-C$_6$ alkyl, —O-C$_1$-C$_6$ alkyl, —NH$_2$, —NH(C$_1$-C$_6$ alkyl), —N(C$_1$-C$_6$ alkyl)$_2$, —CO$_2$H, —CO$_2$(C$_1$-C$_6$ alkyl), —CO$_2$-phenyl, and —CO$_2$-benzyl; and wherein the phenyl and benzyl rings of the R$_2$, —CO$_2$-phenyl, and —CO$_2$-benzyl groups are substituted by 0, 1, 2, or 3 substituents selected from the group consisting of Cl, F, Br, I, OH, C$_1$-C$_6$ alkyl, —O-C$_1$-C$_6$ alkyl, —NH$_2$, —NH(C$_1$-C$_6$ alkyl), and —N(C$_1$-C$_6$ alkyl)$_2$.

13. The compound of claim 1 of Formula IV or Formula V, or a pharmaceutically acceptable salt thereof:

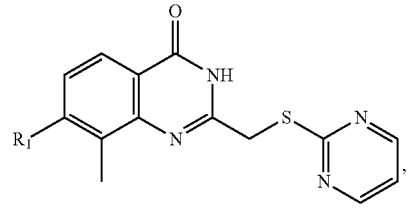

Formula IV

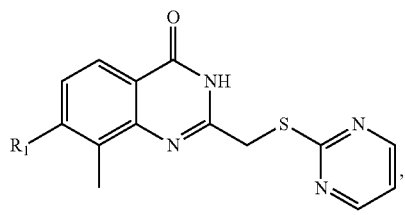

Formula IV(a)

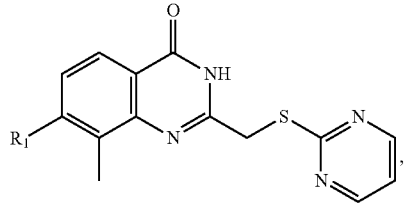

Formula V(a)

wherein R$_1$ is selected from the group consisting of C$_1$-C$_2$ alkyl, C$_2$-C$_3$ alkenyl, and C$_2$-C$_3$ alkynyl.

14. The compound of claim 13, or a pharmaceutically acceptable salt thereof, wherein R$_1$ is selected from the group consisting of CH$_3$, C$_2$-C$_3$ alkenyl, and C$_2$-C$_3$ alkynyl.

15. The compound of claim 13, or a pharmaceutically acceptable salt thereof, wherein R$_1$ is selected from the group consisting of CH$_3$, —CH═CH$_2$, and C$_2$-C$_3$ alkynyl.

16. The compound of claim 13, or a pharmaceutically acceptable salt thereof, wherein R$_1$ is selected from the group consisting of CH$_3$, —CH═CH$_2$, and —C≡C—CH$_3$.

17. The compound of claim 13, or a pharmaceutically acceptable salt thereof, wherein R$_1$ is —C≡C—CH$_3$.

18. A pharmaceutical composition comprising a pharmaceutically effective amount of the compound of claim 13, or a pharmaceutically acceptable salt thereof, and a pharmaceutically acceptable carrier or excipient.

19. A method of sensitizing a cell to a DNA-damaging agent, the method comprising administering to a human in need thereof a pharmaceutically effective amount of the compound of claim 13, or a pharmaceutically acceptable salt thereof, and optionally, wherein the DNA-damaging agent is selected from the group consisting of cisplatin, carboplatin, oxaliplatin, picoplatin, dicycloplatin, eptaplatin, lobaplatin, miriplatin, nedaplatin, satraplatin, triplatin tetranitrate, doxorubicin, daunorubicin, epirubicin, idarubicin, procarbazine, altretamine, bleomycin, carmustine, lomustine, streptozocin, semustine, temozolomide, 5-fluorouracil, capecitabine, floxuridine, gemcitabine, 6-mercaptopurine, 8-azaguanine, fludarabine, cladribine, methotrexate, aminopterin, pemetrexed), ralitrexed, etoposide, aphidicoliin, hydroxyurea, Inotuzumab ozogamicin, cyclophosphamide, chlormethine, Melphalan, Chlorambucil, Ifosfamide, and Bendamustine.

20. A method of treating a protein folding or a protein misfolding disease in a human, the method comprising administering to a human in need thereof a pharmaceutically effective amount of a compound of the compound of claim 13, or a pharmaceutically acceptable salt thereof, and optionally, wherein the protein folding or protein misfolding disease in a human is selected from the group consisting of Huntington's disease, spinobulbar muscular atrophy, Machado-Joseph disease, dentatorubral-pallidoluysian atrophy, spinocerebellar ataxia, Alzheimer's disease, Parkinson's disease, amyotrophic lateral sclerosis, Creutzfeldt-Jakob disease, bovine spongiform encephalopathy, light chain amyloidosis, heavy chain amyloidosis, secondary amyloidosis, aortic medial amyloidosis, ApoA1, ApoAII, ad ApoAIV amyloidosis, insulin amyloidosis, cerebral β-amyloid angiopathy, retinal ganglion cell degeneration in glaucoma, prion diseases, cataracts, tauopathies, frontotemporal lobar degeneration, FTLD-FUS, amyotrophic lateral sclerosis, cerebral autosomal dominant arteriopathy with subcortical infarcts and leukoencephalopathy, Alexander disease, familial amyloidotic neuropathy, senile systemic amyloidosis, serpinopthies, Cystic Fibrosis, and Sickle Cell Disease.

\* \* \* \* \*